(12) United States Patent
Morimoto et al.

(10) Patent No.: US 7,569,690 B2
(45) Date of Patent: Aug. 4, 2009

(54) PROCESS FOR PRODUCING OXYCARBONYL-SUBSTITUTED PIPERAZINE DERIVATIVE

(75) Inventors: Masao Morimoto, Nagoya (JP); Haruyo Sato, Nagoya (JP)

(73) Assignee: Toray Fine Chemicals Co., Ltd. (JP)

( * ) Notice: Subject to any disclaimer, the term of this patent is extended or adjusted under 35 U.S.C. 154(b) by 453 days.

(21) Appl. No.: 10/524,517

(22) PCT Filed: Sep. 2, 2003

(86) PCT No.: PCT/JP03/11204

§ 371 (c)(1),
(2), (4) Date: Feb. 11, 2005

(87) PCT Pub. No.: WO2004/022548

PCT Pub. Date: Mar. 18, 2004

(65) Prior Publication Data

US 2006/0161003 A1 Jul. 20, 2006

(30) Foreign Application Priority Data

Sep. 5, 2002 (JP) ............................. 2002-260376

(51) Int. Cl.
*C07D 241/04* (2006.01)
*C07D 295/00* (2006.01)
(52) U.S. Cl. ...................... 544/358; 544/399
(58) Field of Classification Search ................ 544/358, 544/399; 514/252.12, 255.01
See application file for complete search history.

(56) References Cited

U.S. PATENT DOCUMENTS

2003/0208074 A1* 11/2003 Wu et al. .................... 544/359

2005/0171120 A1* 8/2005 Wu et al. ................ 514/255.04

FOREIGN PATENT DOCUMENTS

| JP | 10-507917 A | 8/1998 |
| JP | 2000-7664 A | 1/2000 |
| JP | 2001-328938 A | 11/2001 |
| WO | WO 96/12492 | * 5/1996 |

OTHER PUBLICATIONS

Kim, et al., N-Benzyloxycarbonyl-2-methylaminothiazoline as a Selective Benzyloxycarbonylating Reagent of Amines, Bull. Korean Chem. Soc., vol. 24, No. 2, 157-58 (2003).*
Bradbury, J.B. et al, "Muscarinic receptor binding and activation of second messengers by substituted N-Methyl-N-[4-(1-azacycloalkyl-2-butnyl]acetamides", Journal of Medicinal Chemistry, vol. 34, 1991, pp. 1073-1079, XP002437848 US p. 1078, col. 1, paragraph 3.
Steward H.W. et al., "Experimental Chemotherapy of Filariasis, IV The Preparation of Derivatives of Piperazine", Journal of Organic Chemistry, vol. 13, 1948, pp. 134-143, XPO02437849 US American Chemistry Society, Washington, DC p. 137, procedure (e).
Graham J. Atwell et al., "Monoprotection of χ,ω-Alkanediamines with the N-Benzyloxcarbonyl Group", Synthesis (Dec. 1984), pp. 1032-1033.
Kazuhiro Kondo et al., "A versatile synthon for chemoselective N-acylation reagents, 2-fluoro-N-mesylaniline", J. Chem. Soc., Perkin Trans. 1 (1998), pp. 2973-2974.
"Protective Groups in Organic Synthesis," John Wiley & Sons Inc., Third Edition (1999), pp. 531-532.
"Yukikagaku-Jikken-no-Tebiki 4—Gosei-Hanno"—[II] (English Translation: Introduction to Experiments of Organic Chemistry 4—Synthetic Reactions [II])—(Kagaku Dojin, 1990), with English translation of p. 24, line 17 to p. 25, line 10.

* cited by examiner

*Primary Examiner*—James O Wilson
*Assistant Examiner*—Erich A Leeser
(74) *Attorney, Agent, or Firm*—DLA Piper LLP (US)

(57) ABSTRACT

If an organic solvent with a water content of 15% or less is used when an oxycarbonyl-substituted piperazine derivative is produced from a piperazine derivative, the piperazine derivative can be oxycarbonylated.

13 Claims, No Drawings

PROCESS FOR PRODUCING OXYCARBONYL-SUBSTITUTED PIPERAZINE DERIVATIVE

TECHNICAL FIELD

This disclosure relates to a process for producing an oxycarbonyl-substituted piperazine derivative by oxycarbonylating a piperazine derivative.

BACKGROUND

Various methods are known as reactions for oxycarbonylating amino groups. As a reaction method for it, in which a piperazine derivative represented by general formula (1) is oxycarbonylated to produce an oxycarbonyl-substituted piperazine derivative represented by general formula (2)

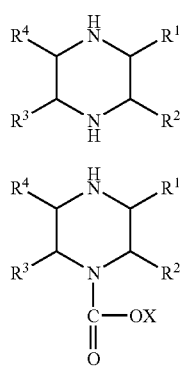

(where $R^1$, $R^2$, $R^3$ and $R^4$ denote, respectively independently, i) a hydrogen atom, ii) an alkyl group with 1 to 4 carbon atoms, iii) an alkoxy group with 1 to 4 carbon atoms, iv) a halogen group, v) a carboxyl group, vi) a carbamoyl group, or vii) an N-alkylcarbamoyl group with 1 to 4 carbon atoms in its alkyl group; X denotes i) an alkyl group with 1 to 4 carbon atoms, ii) an alkenyl group with 2 to 4 carbon atoms, iii) an alkynyl group with 2 to 4 carbon atoms, iv) an aralkyl group not substituted in the aromatic ring, or substituted by an alkyl group with 1 to 4 carbon atoms or by an alkoxy group with 1 to 4 carbon atoms or by a halogen group, or v) an aryl group not substituted in the aromatic ring, or substituted by an alkyl group with 1 to 4 carbon atoms or by an alkoxy group with 1 to 4 carbon atoms or a halogen group; excluding the case where all of $R^1$, $R^1$, $R^3$ and $R^4$ denote a hydrogen atom respectively), the so-called Schotten-Baumann's method for performing a reaction in a mixed solvent of an organic solvent-water under an alkaline condition is employed. Detailed reaction conditions for the method are described in {"Protective Groups in Organic Synthesis," Third Edition (John Wiley & Sons Inc., 1999), p. 531} and {Yukikagaku-Jikken-no-Tebiki 4—Gosei-Hanno—[II] (=Introduction to Experiments of Organic Chemistry 4—Synthetic Reactions [II])—(Kagaku Dojin, 1990), p. 24}. For example, in the former, benzyl chlorocarbonate is used for performing benzyloxy-carbonylation (Z-protection) in a sodium carbonate aqueous solution. Furthermore, in the latter, as an experimental example, the amino groups in kanamycin A sulfate were Z-protected using 1.3 eq. of Z-Cl. The reaction solvent was a mixed solvent of methanol/water=17/83 (ratio by weight). The yield was as low as 64%.

Moreover, there is a report that a reaction for monobenzyloxycarbonylation of a diamine by benzyl chlorocarbonate was performed in water-ethanol-dimethoxyethane solvent (the water content of the solvent=about 50 wt %) while the pH of the system was adjusted in 3.5 to 4.5 {Synthesis, 1032 (1984)}. However, also in this case, when the diamine was ethylene-diamine, the yield was as low as 71%, and it is reported that the yield declined with the increase of carbon atoms.

On the other hand, Reference Example 10 of JP2001-328938A was carried out using 0.25 molar time, based on the amount of 2-methylpiperazine, of Z-Cl in dichloromethane solvent at a very low temperature of −78° C. difficult to achieve industrially in general equipment. In this case, for inhibiting the side reaction by Z-Cl, 2-methylpiperazine more substrative than Z-Cl was used in a large amount for carrying out at a very low temperature. The yield based on the amount of Z-Cl was 85%, while the yield based on the amount of the substrate was 21%. In the case where an expensive substrate like an optically active substance is used, a method of 1 or more in the molar ratio of substrate/Z-Cl is economically disadvantageous. Furthermore, in {J. Chem. Soc., Perkin Trans. 1, 2973 (1998)}, acylation, especially Z-protection, benzoylation, tert-butoxycarbonylation (Boc-protection), etc. are performed using an N-mesyl-N-acylaniline derivative, but since it is necessary to synthesize an oxycarbonylating agent separately, the method cannot be said to be industrially efficient.

So, in the case where a water-soluble piperazine derivative is made to react by a generally publicly known method of a liquid-liquid two-phase system, the yield of the oxycarbonyl-substituted piperazine derivative is as low as less than 50%. It was found that the byproduct in which both the two nitrogen atoms of the piperazine provided as the raw material are substituted by oxycarbonyl groups is produced more than the intended oxycarbonyl-substituted piperazine derivative. Therefore, it is demanded to create a simple method for producing an oxycarbonyl-substituted piperazine derivative at a high yield. It could therefore be advantageous to provide a process for producing an oxycarbonyl-substituted piperazine derivative at a high yield by oxycarbonylating a piperazine derivative.

SUMMARY

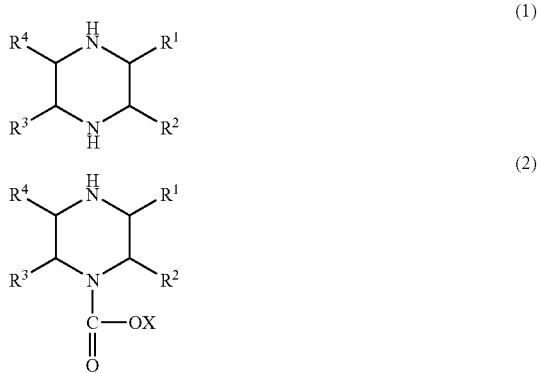

DETAILED DESCRIPTION

A particular method of this reaction will be exemplified.

The piperazine derivative represented by general formula (1)

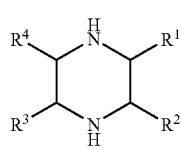

(1)

(where $R^1$, $R^2$, $R^3$ and $R^4$ denote, respectively independently, i) a hydrogen atom, ii) an alkyl group with 1 to 4 carbon atoms, iii) an alkoxy group with 1 to 4 carbon atoms, iv) a halogen group, v) a carboxyl group, vi) a carbamoyl group, or vii) an N-alkylcarbamoyl group with 1 to 4 carbon atoms in its alkyl group; excluding the case where all of $R^1$, $R^2$, $R^3$ and $R^4$ denote a hydrogen atom respectively) is a piperazine derivative substituted by one to four substituent groups. Examples of it include 2-methylpiperazine, 2-ethylpiperazine, 2,3-dimethylpiperazine, 2-methoxypiperazine, 2-isopropoxypiperazine, 2-methoxy-5-n-butoxypiperazine, 2-chloropiperazine, 2-bromopiperazine, 2,6-dichloropiperazine, 2-methyl-3-chloropiperazine, 2-piperadinecarboxylic acid, 2-ethyl-3-piperazinecarboxylic acid, 2-tert-butyl-3-piperazinecarboxylic acid, 2-piperazinecarboxamide, 2-ethyl-3-piperazinecarboxamide, 2-tert-butylcarboxamide, 3-methoxy-2-tert-butylcarboxamide, 2-n-butylcarboxamide, etc. Preferred are 2-methylpiperazine, 2-ethyl-piperazine and 2,3-dimethylpiperazine. More preferred is 2-methylpiperazine. Any of them can also be a racemic modification or optically active substance.

Furthermore, the piperazine derivative can be in a free state or can also form a salt. Examples of it include tartaric acid salts such as p-, p'-ditoluoyltartaric acid (PTTA) salt, o-, o'-ditoluoyltartaric acid (OTTA) salt, dibenzoyltartaric acid (DBTA) salt, and p-, p'-dianisoyl-tartaric acid (DATA) salt, benzoic acid salts such as benzoic acid salt, 3,5-dinitrobenzoic acid salt and 1,3-benzenedicarboxylic acid salt, mineral acid salts such as phenol salts, hydrochloric acid salts, sulfuric acid salts, nitric acid salts and phosphoric acid salts of phenol, nitrophenol, resorcinol, catechol, etc., metal halide salts such as copper tetrachloride salt, copper tetrabromide salt and cobalt trichloride salt, etc. Preferred is a salt of tartaric acid and any of its derivatives, and more preferred is a salt of optically active tartaric acid and any of its derivatives.

The oxycarbonyl-substituted piperazine derivative obtained is represented by the general formula (2)

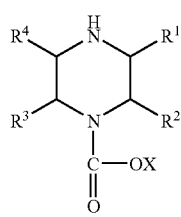

(2)

(where $R^1$, $R^2$, $R^3$ and $R^4$ denote, respectively independently, i) a hydrogen atom, ii) an alkyl group with 1 to 4 carbon atoms, iii) an alkoxy group with 1 to 4 carbon atoms, iv) a halogen group, v) a carboxyl group, vi) a carbamoyl group, or vii) an N-alkylcarbamoyl group with 1 to 4 carbon atoms in its alkyl group; X denotes i) an alkyl group with 1 to 4 carbon atoms, ii) an alkenyl group with 2 to 4 carbon atoms, iii) an alkynyl group with 2 to 4 carbon atoms, iv) an aralkyl group not substituted in the aromatic ring, or substituted by an alkyl group with 1 to 4 carbon atoms or by an alkoxy group with 1 to 4 carbon atoms or by a halogen group, or v) an aryl group not substituted in the aromatic ring, or substituted by an alkyl group with 1 to 4 carbon atoms or by an alkoxy group with 1 to 4 carbon atoms or by a halogen group; excluding the case where all of $R^1$, $R^2$, $R^3$ and $R^4$ denote a hydrogen atom respectively), and it is preferred that X denotes a tert-butyl group or benzyl group. Examples include 1-methoxycarbonyl-2-methylpiperazine, 1-methoxycarbonyl-3-methylpiperazine, 2-ethyl-1-methoxycarbonylpiperazine, 1-ethoxycarbonyl-2-methylpiperazine, 1-tert-butoxycarbonyl-2-methylpiperazine, 1-tert-butoxycarbonyl-3-methylpiperazine, 1-tert-butoxycarbonyl-2,3-dimethylpiperazine, 1-tert-bu-toxycarbonyl-2-methoxy-3-methylpiperazine, 1-vinyloxycarbonylpiperazine, 1-vinyloxvcarbonvl-2-methylpiperazine, 1-vinyloxvcarbonvl-3-methylpiperazine, 1-allyloxycarbonylpiperazine, 1-allyloxycarbonyl-2-methylpiperazine, 1-allyloxycarbonyl-3-methylpiperazine, 1-methylpropionyloxycarbonyl-2-methylpiperazine, 1-benzyloxycarbonyl-2-piperazine, 1-benzyloxycarbonyl-3-methylpiperazine, 1-benzyloxycarbonyl-2,3-dimethylpiperazine, 1-benzyloxycarbonyl-3,5-dimethylpiperazine, 1-benzyloxycarbonyl-3-methoxypiperazine, 1-(p-methylphenylmethyl)oxycarbonyl-2-methylpiperazine, 1-(p-methylphenylmethyl)oxycarbonyl-3-methylpiperazine, 1-phenoxy-carbonyl-2-methylpiperazine, 1-phenoxycarbonyl-2-methylpiperazine, 1-phenoxycarbonyl-3-methylpiperazine, 1-phenoxycarbonyl 2,5-dimethylpiperazine, etc. These compounds can be synthesized from general formula (1), and can be either racemic modifications or optically active substances.

As the reagent used for oxycarbonylation, those described in {"Protective Groups in Organic Synthesis" Third Edition (John Wiley & Sons Inc., 1999), p. 531} can be used. Particularly those having a structure represented by general formula (3) or general formula (4):

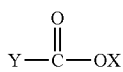

(3)

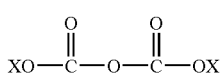

(4)

(where X denotes i) an alkyl group with 1 to 4 carbon atoms, ii) an alkenyl group with 2 to 4 carbon atoms, iii) an alkynyl group with 2 to 4 carbon atoms, iv) an aralkyl group not substituted in the aromatic ring, or substituted by an alkyl group with 1 to 4 carbon atoms or by an alkoxy group with 1 to 4 carbon atoms or by a halogen group, or v) an aryl group not substituted in the aromatic ring, or substituted by an alkyl group with 1 to 4 carbon atoms or by an alkoxy group with 1 to 4 carbon atoms or by a halogen group) can be preferably used, and include chlorocarbonate esters typified by methyl chlorocarbonate, ethyl chlorocarbonate, vinyl chlorocarbonate, allyl chlorocarbonate, phenyl chlorocarbonate, benzyl chlorocarbonate, p-bromobenzyl chlorocarbonate, etc., and dicarbonate esters such as dimethyl dicarbonate, diethyl dicerbonate, di-tert-butyl dicarbonate (DiBoc), diphenoxy dicarbonate and dibenzyloxy dicarbonate. Preferred are chlorocarbonate esters typified by benzyl chlorocarbonate and ethyl chlorocarbonate, and di-tert-butyl dicarbonate (DiBoc).

The amount of it added is usually 0.9 to 1.2 moles, preferably 0.95 to 1.1 moles, more preferably 0.98 to 1.05 moles based on the amount of the piperazine derivative provided as the raw material. In the case of 1 mole or more, the reagent is more likely to be bound to the two nitrogen atoms of the piperazine derivative, and on the other hand, in the case of less than 1 mole, the piperazine derivative is likely to remain as an unreactive raw material. Therefore, it is preferred to change the amount used in response to each purpose.

The conditions for adding the reagent are not especially limited. In general, dropwise addition is performed in a temperature range from −25 to 60° C., preferably in a range from −10 to 40° C., more preferably from −5 to 30° C. The addition time period can be adjusted in response to the temperature and is not especially limited. However, it is usually from 1 to 12 hours.

The organic solvent used for the reaction can be soluble or insoluble in water. However, an organic solvent of 1 wt % or more in the mutual solubility with water at 20° C. is preferred.

Furthermore, considering the reaction yield, it is preferred that the water content of the organic solvent is lower, and at a water content of 15 wt % or less, a virtually satisfactory result can be obtained. For this reason, it is necessary that the water content of the organic solvent is 15 wt % or less. If the water content is more than 15 wt %, there arises a problem, since the reaction yield of the oxycarbonyl pipe razine derivative obtained by oxycarbonylating the piperazine derivative is remarkably lowered.

Meanwhile, the water content of the organic solvent used for the reaction can be obtained using a Karl Fischer water content meter.

The water content does not mean the rate of only the water homogeneously dissolved in the organic solvent, but means the rate of the water forming a two-phase system due to separation from the organic solvent. For example, in a water-toluene system, water-1-butanol system or the like, water can exist separately in the lower layer while the organic solvent can exist in the upper layer, and such a case is included. In this case, the water contents in the respective upper and lower layers can be individually measured, and the water content of the organic solvent can be calculated from the following calculation formula: (Water content of the organic solvent) =100×(Water content of the upper layer×Weight of the upper layer+Water content of the lower layer×Weight of the lower layer)/(Weight of the upper layer+Weight of the lower layer).

Examples of the organic solvent include alcohols such as methanol, ethanol, 1-propanol, isopropanol, 1-butanol, 2-butanol, isobutanol, 1-pentanol, 2-pentanol and isopentanol, ethers such as diethyl ether, diisopropyl ether, di-n-propyl ether, 1,4-dioxane, 1,3-dioxane and methyl-tert-butyl ether, ketones such as acetone, methyl ethyl ketone, methyl isobutyl ketone, 2-pentanone and 3-pentanone, aromatic hydrocarbons such as benzene, toluene, ethylbenzene, p-xylene, m-xylene and p-xylene, and aliphatic hydrocarbons such as pentane, n-hexane, isohexane, cyclohexane and octane. Preferred are alcohols such as methanol, ethanol, 1-propanol, isopropanol, 1-butanol, 2-butanol, isobutanol, 1-pentanol, 2-pentabol and isopentanol, and ethers such as diethyl ether, diisopropyl ether, di-n-propyl ether, 1,4-dioxane, 1,3-dioxane and methyl-tert-butyl ether. More preferred are alcohols such as methanol, ethanol, 1-propanol, isopropanol, 1-butanol, 2-butanol, isobutanol, 1-pentanol, 2-pentanol and isopentanol. Further more preferred are alcohols such as methanol, ethanol, 1-propanol, isopropanol, 1-butanol, 2-butanol and isobutanol. Any one of these solvents can be used, or plural organic solvents can also be used as a mixed solvent. Furthermore, a solvent containing water can be a homogeneous solution or can also be separated in phase. However, the state of a homogeneous solution is preferred.

The amount of the organic solvent used is not especially limited, and is used to ensure that the concentration of the piperazine derivative before adding the reagent is from 5 to 20 wt %.

Meanwhile, usually in oxycarbonylation, a basic compound is often added for capturing hydrochloric acid produced as a byproduct. Also, the addition of a basic compound is an effective means. That is, a basic compound can be made to coexist in the reaction system when the piperazine derivative is oxycarbonylated.

The nitrogen-containing compound made to coexist is not especially limited. Examples include pyridine, α-picoline, β-picoline, γ-picoline, 2-ethylpyridine, 3-ethylpyridine, 4-ethylpyridine, 2-n-propylpyridine, 3-n-propylpyridine, 4-n-propylpyridine, 2-isopropylpyridine, 2-phenylpyridine, 2-vinylpyridine, 3-aminopyridine, 2-hydroxypyridine, 2-methoxypyridine, 2-chloropyridine, 3-fluoropyridine, 4-bromopyridine, 3-iodopyridine, 2-formylpyridine, 3-acetylpyridine, 2-pyridinecarboxylic acid, methyl 3-pyridinecarboxylate, 3-pyridinecarboxylic acid amide, 2-cyanopyridine, 3-nitropyridine, pyrrole, indole, pyrazole, isoxazole, isothiazole, indazole, imidazole, oxazole, thiazole, benzimidazole, quinoline, isoquinoline, pyridazine, pyrimidine, pyrazine, quinoxaline, carbazole, α-aminonaphthalene, β-amino-naphthalene, aniline, 2,6-lutidine, trimethylamine, etc. Preferred are aromatic nitrogen-containing compounds, and further preferred are aromatic nitrogen-containing compounds with a pKa of 7 or less. Especially preferred are pyridine and its derivatives.

The pKa values of some nitrogen-containing compounds are shown below. Handbook of Chemistry, Eleventh Edition (McGRAW-HILL Book Company, 1973) and Hetero-kan Kagobutsu-no Kagaku (=Chemistry of Heterocyclic Compounds) (Kodansha Scientific, 1988) show 5.23 for pyridine, 6.62 for 2-methoxypyridine, 0.72 for 2-chloropyridine, 2.5 for pyrazole, 10.7 for trimethylamine and 7.76 for triethanolamine.

The reason why an aromatic nitrogen-containing compound is preferred is that it has a capability of activating an oxycarbonylating agent to a medium extent. That is, since an aromatic nitrogen-containing compound is weaker in basicity than an aliphatic nitrogen-containing compound typified by trimethylamine, it does not activate the oxycarbonylating agent excessively. So, it can be said that a side reaction to oxycarbonylate both the two nitrogen atoms of the piperazine derivative simultaneously is hard to occur.

Usually the basic compound can be made to coexist in the piperazine derivative solution before adding the oxycarbonylating agent, or it can also be mixed with the oxycarbonylating agent for addition to the piperazine derivative solution.

The amount used of a general basic compound is from 0.1 to 1.5 molar times, preferably 0.3 to 1.3 molar times, more preferably 0.5 to 1.2 molar times based on the amount of the piperazine derivative. The oxycarbonylation reaction in the coexistence of the basic compound can be carried out in quite the same way as in an ordinary method, except the operation of letting the basic compound coexist.

Meanwhile, the piperazine derivative provided as the raw material used for oxycarbonylation described above can be either a racemic modification or an optically active substance, and either of them produced by any of various methods can be used.

Above all, an optically active piperazine derivative useful, for example, as a raw material of a drug can be produced from a piperazine derivative provided as a chemically synthesized racemic modification, using a method such as optical resolution.

The following exemplifies the principle in the process for producing an optically active piperazine derivative.

For example, at first, a racemic piperazine derivative and an optically active acid compound (hereinafter called an optical resolving agent) are made to form diastereomer salts. Then, while the salt concentrations, crystallization solvent and crystallization temperature are adjusted, the solubility difference between the diastereomer salts can be used for separation into R-isomer and S-isomer. The diastereomer salts obtained like this can be converted into highly pure products with an optical purity of 99% ee or more by repeating crystallization. The obtained salts can be decomposed using an acid or alkali to recover the intended optically active substance from the diastereomer salts.

Furthermore, as a particular method, a method of producing optically active 2-methylpiperazine will be exemplified. An optical resolution method using optically active tartaric acid as an optical resolving agent is known. That is, equimolar amounts of (±)-2-methylpiperazine and optically active tartaric acid are made to reach with each other, to produce 2-methylpiperazine monotartaric acid salt as two diastereomer salts, and the difference between their solubilities in a mixes solvent is used for optical resolution in this method {J. Med. Chem., 33, 1645, (1990)}.

As similar methods, various publicly known examples can be enumerated. For example, JP1-149775A describes a performing method using 1 to 10 molar times, preferably 2 molar times, based on the amount of (±)-2-methylpiperazine, of optically active tartaric acid. Furthermore, Japanese Patent 3032547 describes a method in which 2 molar times, based on the amount of (±)-2-methylpiperazine, of optically active tartaric acid is used in a diluted condition of 5 to 10 as the ratio by weight of supplied water/(±)-2-methylpiperazine. Furthermore, publicly known are a report concerning a continuous process of collecting optically active 2-methylpiperazine monotartaric acid salt as a slightly soluble salt by filtration and then collecting the other optically active 2-methylpiperazine ditartaric acid salt as a slightly soluble salt from the remaining mother liquor (JP2001-131157A) and a report concerning a method of letting (±)-2-methylpiperazine and an optically active dibasic acid react with each other in a solvent for obtaining a salt of the optical resolution product of 2-methylpiperazine and the optically active dibasic acid, wherein an optically inactive acid is made to coexist in the reaction system (JP2002-80459A). The optically inactive acid in the latter is particularly an organic acid such as acetic acid or a mineral acid such as hydrochloric acid, judging from the examples, and the use of it allows the amount of the resolving agent used to be decreased.

In these methods, in the case where D-tartaric acid is used to form optically active 2-methylpiperazine monotartaric acid salt, (−)-2-methylpiperazine, i.e., (S)-2-methylpiperazine can be obtained from the slightly soluble salt. On the other hand, in the case where L-tartaric acid is used, similarly (+)-2-methylpiperazine, i.e., (R)-2-methylpiperazine can be obtained.

Furthermore, as a method of using an optically active resolving agent other than optically active tartaric acid, a method of using a resolving agent such as an L-aspartic acid derivative is reported (Japanese Patent 2823679). As another method, a method of using a chiral phosphoate that is an inclusion compound {Chem. Lett., 513 (1988)} is reported.

As described above, various reports exists for optically active 2-methylpiperazine, and any of the methods can be used to produce the piperazine derivative used for oxycarbonylation.

The piperazine derivative can be used in any of various forms such as liquid or solid, and especially in the latter, any of various forms ranging from mass to pellets can be used. Even in the case where any of racemic piperazine derivative is made into an optically active substance by an optical resolution method, a piperazine derivative with either property of liquid or solid can be used. Furthermore, the piperazine derivative can be used in a free state or in a state of a salt with an optical resolving agent for the oxycarbonylation reaction.

As an optical resolving agent, an optically active carboxylic acid or any of its derivatives or an optically active amino acid or any of its derivative can be used. Examples include optically active tartaric acid such as L-tartaric acid or D-tartaric acid, and optically active tartaric acid derivatives such as O,O'-di-p-toluoyl-L-tartaric acid, O,O'-di-o-toluoyl-L-tartaric acid, O,O'-dibenzoyl-L-tartaric acid, O,O'-di-p-anisoyl-L-tartaric acid, O,O'-di-p-toluoyl-D-tartaric acid, O,O'-di-o-toluoyl-D-tartaric acid, O,O'-dibenzoyl-D-tartaric acid and O,O'-di-p-anisoyl-D-tartaric acid, optically active malic acid such as L-malic acid or D-malic acid, optically active mandelic acid such as R-mandelic acid or L-mandelic acid, optically active aspartic acid such as L-aspartic acid or D-aspartic acid, optically active aspartic acid derivatives such as N-benzoyl-L-aspartic acid, N-benzoyl-D-aspartic acid, N-p-toluenesulfonyl-L-aspartic acid and N-p-toluenesulfonyl-D-aspartic acid, etc. Preferred are optically active carboxylic acids and their derivatives, and especially preferred are optically active tartaric acid and its derivatives. The optically active tartaric acid can be any of various products ranging from natural products to synthetic products, and can also be either D-tartaric acid or L-tartaric acid.

The amount of the optically active resolving agent used here is decided in reference to the the mole balance between an acid and a base. Since the piperazine derivative is a diacidic base, in the case where the optically active resolving agent is a dibasic acid, the amount of the optically active resolving agent used is usually from 0.1 to 1.5 molar times, preferably from 0.2 to 1.3 molar times, and more preferably from 0.3 to 1.2 molar times based on the amount of the piperazine derivative.

In the production of an optically active piperazine derivative, if the method of letting an optically inactive acid is made to coexist, described in JP2002-80459A, is used, the amount of the optically active resolving agent used can be decreased. If it is in this range, the amount of waste generated according to the method described in any of publicly known documents can be decreased very advantageously also in view of cost.

As the optically inactive acid, a lower carboxylic acid or mineral acid can be used.

A lower carboxylic acid means a carboxylic acid with 1 to 4 carbon atoms, and examples include acetic acid, propionic acid and butyric acid. Acetic acid is preferred. Furthermore, the mineral acid can be hydrochloric acid, sulfuric acid, hydrobromic acid, hydroiodic acid, etc. Hydrochloric acid and sulfuric acid are preferred.

The amount of the optically inactive acid used is usually from 0.1 to 2.0 molar times, preferably from 0.3 to 1.5 molar times, more preferably from 0.5 to 1.0 molar time based on the amount of the piperazine derivative.

Any of various solvents can be used for optical resolution, but a water-containing solvent is preferred. It is preferred that the water content of the solvent is 50 wt % or more. More preferred is 80 wt % or more, and it is especially preferred that the solvent consists of water only. As the component other than water in the water-containing solvent, any of various organic solvents can be used. An organic solvent of 3 wt % or more in the mutual solubility with water at 20° C. is preferred. In the case where the mutual solubility is 3 wt % or less, if diastereomer salts are formed by heat dissolution for optical resolution, the system may become heterogeneous, and the optical purity of the diastereomer salts obtained by crystallization may become very low. Examples of the organic solvent with a mutual solubility of 3 wt % or more include alcohols such as methanol, ethanol, 1-propanol, isopropanol, 1-butanol, 2-butanol and isobutanol, ethers such as methyl-t-butyl ether, tetrahydrofuran and 1,4-dioxane, ketones such as acetone, methyl ethyl ketone and methyl isobutyl ketone, etc. Preferred are methanol, ethanol, 1-propanol and isopropanol, and especially preferred is methanol.

In general as the solvent system, it is desirable to select a system ensuring that the ratio of the solubilities of the two diastereomer salts formed from the racemic piperazine derivative and the optical resolving agent becomes 3 or more.

For example, if the piperazine derivative is 2-methyl piperazine and the optical resolving agent is optically active tartaric acid, then the following water-methanol mixed solvent systems can be referred, for example, as described below.

TABLE 1

|  | Water content (wt %) | | | |
| --- | --- | --- | --- | --- |
|  | 50 | 60 | 80 | 100 |
| Solubility (S-D salt) | 0.51 | 0.81 | 1.9 | 5.0 |
| Solubility (R-D salt) | 1.7 | 4.1 | 26.4 | 63.6 |
| Solubility ratio (g/g) | 3.3 | 5.1 | 13.9 | 12.7 |

The value of a solubility in the table expresses the amount dissolved per 100 g of the solvent (g/100 g solvent), and the solubility ratio expresses Solubility (R-D salt)/Solubility (S-D salt).

In Table 1, the S-D salt means a salt of (S)-2-methylpiperazine and D-tartaric acid, and the R-D salt means a salt of (R)-2-methylpiperazine and D-tartaric acid. Preferred is a water-methanol mixed solvent system of 3 or more in the solubility ratio, i.e., in the value of (Solubility of R-D salt)/(Solubility of S-D salt) and of 50 wt % or more in water content. A more preferred water content is 60 wt % or more, and a further more preferred water content is 80 wt % or more. That is, it is advantageous that the solvent in a system in which 2-methylpiperazine is optically resolved using optically active tartaric acid mainly contains water, considering the difference between the solubilities of the two salts produced in the system.

In the case where an optically active piperazine derivative is produced by an optical resolution method, the amount of the solvent used greatly depends on the solubilities of the diastereomer salts in the solvent used.

Therefore, the amount of the solvent used and a particular optical resolution method are described below in reference to a system consisting of racemic 2-methylpiperazine and water solvent.

Usually, the amount of the water solvent used is 0.3 to 10.0 times by weight, preferably 0.4 to 8 times by weight, more preferably 0.5 to 4.0 times by weight based on the amount of racemic 2-methylpiperazine. If the amount of the solvent used is too large, the salt concentration declines, and also the amounts of the acquired diastereomer salts decline to lower productivity. On the other hand, if it is too small, the decline of stirring operation efficiency and the degradation of quality such as optical purity occur. Especially in a range from 0.5 to 4.0 times by weight, the amount of the recycled solvent can be minimized, and the loss at the time of recovery or waste water can be reduced advantageously in view of industrialization.

As for the supplying method, the racemic 2-methylpiperazine, optically active resolving agent and lower carboxylic acid or mineral acid can be supplied simultaneously or can be supplied sequentially with the lapse of time. Furthermore, the racemic 2-methylpiperazine and the optically active resolving agent can be dissolved in the solvent beforehand, being followed by mixing, or either one only can be dissolved in the solvent, being followed by addition. A method advantageous in view of operation efficiency can be employed. Moreover, the temperature is not especially limited either, and any of various methods can be employed. In general, the heating and aging temperature is in a range from 40 to 100° C. For example, the racemic 2-methylpiperazine and the optically active resolving agent can be dissolved into water respectively separately, being followed by mixing, and acetic acid can be added, being followed by heating up to 70 to 80° C. Otherwise, the racemic 2-methylpiperazine can be dissolved into water, being followed by heating up to 70 to 80° C., and subsequently an optically active resolving agent aqueous solution and acetic acid can be added in this order. Furthermore, the racemic 2-methylpiperazine, optically active resolving agent, acetic acid and water can also be mixed, being followed by heating up to 70 to 80° C. In this case, the state of the reaction system varies depending on the amount of the solvent used, and either a slurry or a homogeneous solution can be formed. A homogeneous solution is preferred. In the case of a homogeneous solution, it is cooled, and seed crystals are added, being followed by sufficient aging and further cooling. The temperature is generally from 0 to 30° C., preferably from 5 to 25° C. In the case of a slurry, it is necessary to heat to a solvent reflux temperature, and to age at the temperature for a sufficient time period, generally from 0.5 to 12 hours, preferably from 1 to 12 hours.

If the optically active 2-methylpiperazine/optically active resolving agent salt obtained as described above is recrystallized, optically active 2-methylpiperazine with a high optical purity of 99.0% ee or more can be obtained. Furthermore, considering the recycling operation, it is preferred that the solvents used for twice optical resolution are identical in composition. In this case, the adjustment of solvent composition for recycled use is not required to allow simple and quick operation very significantly as an industrial process.

The diastereomer salts of an optical active piperazine derivative and an optical resolving agent can be used in a state of salts for the oxycarbonylation reaction, but the salts can also be decomposed to use the optically active piperazine derivative in a free state for the oxycarbonylation.

The precipitated diastereomer salt can be separated from the diastereomer salt in the mother liquor by filtration operation. In general as a method for recovering the optically active nitrogen-containing compound from the diastereomer salt isolated as crystals, a method of extracting in an alkaline aqueous solution using an organic solvent is publicly known.

Concretely reported are a method of adding a very excessive amount of a highly concentrated sodium hydroxide aqueous solution to the diastereomer salt for extraction using an organic solvent such as diethyl ether or benzene {Journal of American Chemical Society, 81, 290 (1959)}, and a method of adding an excessive amount of a highly concentrated sodium hydroxide aqueous solution to the diastereomer salt for causing an amine layer to be separated, collecting the amine layer, removing the water contained in the amine layer using, for example, sodium hydroxide, repeating the operation, and distilling {Canadian Journal of Chemistry, 54, 2639, (1976)}. The bases used in these publicly known techniques are alkali metal hydroxides such as sodium hydroxide and potassium hydroxide, and after salt decomposition, a water soluble amine is recovered by means of extraction or distillation.

Especially in the method of recovering optically active 2-methylpiperazine from the diastereomer salt of optically active 2-methylpiperazine and optically active tartaric acid, obtained by an optical resolution method using optically active tartaric acid, sodium hydroxide and potassium hydroxide are generally used.

For example, in JP3-279375A and Japanese Patent 3032547, sodium hydroxide is used to recover (+)-2-methylpiperazine (the total yield in the crystallization step to the salt decomposition step is 57%). Furthermore, in JP2002-80459, 2.6 molar times, based on the amount of the diastereomer salt, of sodium hydroxide is used for salt decomposition, and distillation under reduced pressure is performed to obtain (R)-2-methylpiperazine. The total yield in the salt decomposition step to the distillation step is 71.0%, and if the distillation yield is assumed to be 90%, the yield in the salt decomposition step is 78.8%. Still furthermore, JP2001-131157A reports cases of using potassium hydroxide for salt decomposition, and the amount of it used was in a wide range from 0.89 to 14.4 molar times based on the amount of the diastereomer salt. The yields in the salt decomposition step were from 71 to 75%.

Moreover, as the method for recovering an optically active amine from the diastereomer salt formed from the optically active amine and an optically active carboxylic acid or optically active sulfonic acid, known is a method of performing contact in the presence of an alcohol solution containing 6 to 50 wt % of water and an alkali metal hydroxide and isolating the free amine from the alcohol layer (Japanese Patent 3312459). In the examples of the patent, sodium hydroxide is added to the salt of optically active 2-methylpiperazine and N-benzenesulfonyl-L-aspartic acid or to the salt of 3-hydroxypyridine and p-toluenesulfonyl-L-phenylalanine in an alcohol solvent containing 7 wt % of water, for recovering an optically active nitrogen-containing compound at a high recovery rate of 97% or more.

In addition, Japanese Patent 3312454 reports a method of bringing an inorganic alkali into contact with the crystals of the salt of an optically active amine and optically active tartaric acid in an alcohol solution with 5 to 40 wt % of water coexisting, and recovering the optically active tartaric acid as an inorganic alkali salt. In the examples of this method, the salt of optically active diaminocyclohexane and optically active tartaric acid, the salt of optically active 1,2-diaminopropane and optically active tartaric acid, or the salt of optically active 1-phenylethylamine and optically active tartaric acid is decomposed in an alcohol solvent with a water content 4 to 14 wt % using sodium hydroxide or potassium hydroxide, and an optically active nitrogen-containing compound is recovered at a high recovery rate of 98% or more.

As described above, the method of using an alkali metal hydroxide typified by sodium hydroxide or potassium hydroxide for salt decomposition and subsequently recovering an optically active piperazine derivative by a method such as extraction can be carried out according to the above-mentioned patent.

Furthermore, in the case where the diastereomer salt of an optically active piperazine derivative and optically active tartaric acid is decomposed using an alkaline earth metal salt, an optically active piperazine derivative can be recovered according to a principle different from that working in the method of using an alkali metal salt. That is, an alkaline earth metal salt of optically active tartaric acid is low in solubility and is precipitated as crystals. That is, in the case where an alkaline earth metal salt is used, the optically active piperazine derivative exists in the mother liquor, and the optically active tartaric acid as an optical resolving agent can be separated as crystals. If this method is used, the extraction method is not necessary, and furthermore in principle, a recovery rate of 100% can be achieved.

The solubilities of metal tartrates in water are shown below as a scientific ground.

The solubilities of alkaline earth metal tartrates obtained when alkaline earth metal hydroxides are used for salt decomposition are 1.22% with magnesium tartrate (26° C.), 0.029% with calcium tartrate (25° C.), 0.18% with strontium tartrate (25° C.) and 0.028% with barium tartrate (21° C.), showing all of them are slightly soluble salts.

On the other hand, the solubilities of alkali metal tartrates obtained when alkali metal hydroxides are used for salt decomposition are 30% with sodium tartrate (24° C.) and 40% with potassium tartrate (15.6° C.), showing they are soluble salts.

Therefore, since the alkali metal tartrate generated when an alkali metal hydroxide is used is dissolved in water, it is virtually impossible to separate from the optically active piperazine derivative in a solvent containing 50 wt % or more of water.

On the other hand, it can be seen that in the case where the alkaline earth metal salt is used, the separation from the optically active piperazine derivative is easy.

As described above, when the diastereomer salt of an optically active piperazine derivative and optically active tartaric acid is decomposed, an alkali metal salt and an alkaline earth metal salt can be used. Examples of the former include sodium hydroxide and potassium hydroxide.

On the other hand, in the case where the optical resolving agent is optically active tartaric acid, the method of using an alkaline earth metal is more advantageous.

The alkaline earth metal salt used is not especially limited, and it can be typified by alkaline earth metal hydroxides, halides, sulfates, etc. Examples include hydroxides such as magnesium hydroxide, calcium hydroxide, strontium hydroxide and barium hydroxide, chlorides such as magnesium chloride, calcium chloride, strontium chloride and barium chloride, bromides such as magnesium bromide, calcium bromide, strontium bromide and barium bromide, sulfates such as magnesium sulfate, calcium sulfate, strontium sulfate and barium sulfate, and carbonates such as magnesium carbonate, calcium carbonate, strontium carbonate and barium carbonate. Preferred are hydroxides, chlorides and sulfates. Especially preferred are hydroxides and sulfates, and further preferred are hydroxides. Especially preferred is calcium hydroxide. The form of calcium hydroxide is not especially limited, and can be powdery or granular, or can also be a slurry of water, etc.

The amount of the alkaline earth metal salt used is from 0.5 to 3.0 molar times, preferably from 0.8 to 2.0 molar times, and more preferably from 1.0 to 1.5 molar times based on the amount of the optically active tartaric acid in the salt to be decomposed, of an optically active piperazine derivative and optically active tartaric acid.

The time when the alkaline earth metal salt is added is not especially limited. It can be added to the aqueous solution of the salt of an optically active piperazine derivative and optically active tartaric acid, or the salt of an optically active piperazine derivative and optically active tartaric acid can also be added into a water slurry of calcium hydroxide. Furthermore, the alkaline earth metal salt is added usually in a range from 0 to 90° C., and in view of operation efficiency and safety, it is desirable to add at near the room temperature.

In the case where the piperazine derivative is soluble in water, it is usually essential to perform salt decomposition in a solvent containing 50 wt % or more of water. The amount of the solvent used is 1 to 10 times by weight, preferably 1 to 7 times by weight, more preferably 2 to 5 times by weight based on the amount of the salt of an optically active nitrogen-containing compound and optically active tartaric acid. If the amount of the solvent is too small, the concentration of the alkaline earth metal salt of optically active tartaric acid generated by salt decomposition in the slurry is so high as to result in insufficient stirring, hence insufficient salt decomposition dangerously. Furthermore, if the amount of the solvent is too large, an economic disadvantage arises in view of the production efficiency since the supplied amount of the salt of an optically active piperazine derivative and optically active tartaric acid is decreased.

On the other hand, in the case where the piperazine derivative is slightly soluble in water, the optically active piperazine derivative liberated by salt decomposition can be extracted using an organic solvent into the organic solvent layer. Examples of the organic solvent include aromatic hydrocarbons such as benzene, toluene, o-xylene, m-xylene, p-xylene, ethylbenzene, n-propylbenzene, isopropylbenzene and mesytilene, aliphatic hydrocarbons such as n-pentane, n-hexane, n-heptane, n-octane, n-nonane and n-decane, alcohols such as 1-butanol, 2-butanol, isobutanol, 1-pentanol, 2-pentanol, 3-pentanol and isopentanol, ethers such as diethyl ether, di-n-propyl ether, diisopropyl ether, methyl-tert-butyl ether and tetrahydrofuran, and ketones such as methyl ethyl ketone, 2-pentanone, 3-pentanone and methyl isobutyl ketone. Preferred are aromatic hydrocarbons and alcohols. In this case, if extraction operation is repeated, the piperazine derivative recovery rate can be enhanced.

The salt decomposition is usually performed in a range from about room temperature to 100° C., preferably in a range from 30 to 100° C., and more preferably in a range from 50 to 100° C. If the temperature is too low, the salt decomposition may be insufficient dangerously. Usually the time period needed for salt decomposition is from 1 to 24 hours. If the time is longer, the salt decomposition yield is higher but less advantageous in view of productivity. Usually it is desirable to perform in a range from 1 to 12 hours.

Meanwhile, the oxycarbonyl piperazine derivative produced by oxycarbonylation contains the impurities represented by general formulae (5) to (8).

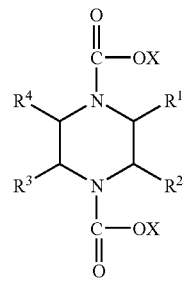

(5)

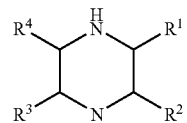

(6)

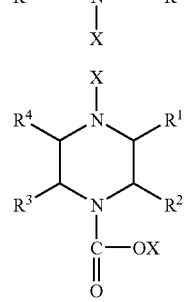

(7)

XOH (8)

The purity of the oxycarbonyl-substituted piperazine derivative may be as very low as 90 liquid chromatography area % in purity as the case may be, due to the ingress of the piperazine derivatives and alcohol represented by general formulae (5) to (8). The piperazine derivative represented by the general formula (5) is the impurity generated by a side reaction in which both the two nitrogen atoms are oxycarbonylated. The piperazine derivatives represented by the general formula (6) and the general formula (7), are the impurities estimated to have been produced through decarboxylation of oxycarbonyl substituent groups. Furthermore, the alcohol represented by the general formula (8) is estimated to be the impurity produced by hydrolyzing the oxycarbonylating agent. That is, the oxycarbonyl-substituted piperazine derivative represented by the general formula (2) obtained by oxycarbonylating the piperazine substitution product represented by the general formula (1) according to a general method contains the impurities represented by the general formulae (5) to (8). So, only a low pure oxycarbonyl-substituted piperazine derivative with a purity of 90 liquid chromatography area % or less can be obtained.

However, the obtained oxycarbonyl-substituted piperazine derivative can be easily converted into a highly pure oxycarbonyl-substituted piperazine derivative by applying a refining step typified by crystallization, washing and/or distillation.

In the case where the obtained oxycarbonyl-substituted piperazine derivative is solid, it can be refined by ordinary crystallization. Furthermore, in the case where the oxycarbonyl substituent group is unstable in an acid like a tert-butoxycarbonyl group, refining by crystallization is desirable. On the other hand, in the case where the oxycarbonyl-substituted piperazine derivative is liquid or in the case where the oxycarbonyl substituent group is stable in an acid like a benzyloxycarbonyl group, the following washing step can be used for refining.

At first a particular method for the washing step will be described.

Among the four impurities represented by the general formulae (5) to (8) produced in the synthesizing step, the piperazine derivative represented by the general formula (5) and the alcohol represented by the general formula (8) are neutral compounds, and if an organic solvent is used for washing, they can be relatively easily removed from the oxycarbonyl-substituted piperazine derivative represented by the general formula (2).

Concretely, an acid is added to the reaction solution containing the oxycarbonyl-substituted piperazine derivative represented by the general formula (2), to make an acid aqueous solution, for converting the oxycarbonyl-substituted piperazine derivative into an acid salt. In this method, if an organic solvent is added and stirring is performed, then the hydrochloride is distributed into the water layer, causing the impurities represented by the general formula (5) and the general formula (8) to be extracted into the organic solvent layer for removal from the reaction solution containing the oxycarbonyl-substituted piperazine derivative.

The method for preparing the acid aqueous solution is not especially limited, but simple is a method of adding a mineral acid into the synthetic reaction solution containing the oxycarbonyl-substituted piperazine derivative represented by the general formula (2), for obtaining the solution. As the mineral acid, for example, hydrochloric acid or sulfuric acid can be preferably used, and the addition is made with the pH of the reaction solution kept at 3 or less. If the pH is large, the oxycarbonyl-substituted piperazine derivative represented by the general formula (2) is less likely to form an acid salt correspondingly, and so it is distributed into the organic solvent during washing, causing the recovery rate to decline.

Furthermore, the concentration of the oxycarbonyl-substituted piperazine derivative in the acid aqueous solution is usually in a range from 5 to 40 wt %, preferably in a range from 10 to 30 wt %, more preferably in a range from 15 to 25 wt %.

The organic solvent used in the washing step is not especially limited if it is industrially available, but considering the recovery rate of the oxycarbonyl-substituted piperazine derivative at the time of extraction, an organic solvent of 10% or less in the mutual solubility with water at 20° C. is preferably used. Examples include aromatic hydrocarbons such as toluene, benzene, o-xylene, m-xylene, p-xylene and ethylbenzene, alcohols such as 1-butanol, 2-butanol isobutanol, 1-pentanol, 2-pentanol, 3-pentanol, 1-hexanol and cyclohexanol, ethers such as diethyl ether, ethyl propyl ether, ethyl isopropyl ether, isopropyl ether, isobutyl methyl ether, tert-butyl methyl ether and tetrahydrofuran, ketones such as 3-pentanone, tert-butyl methyl ketone, 2-hexanone, 3-hexanone and 2-heptanone. Preferred are aromatic hydrocarbons and alcohols, and more preferred are aromatic hydrocarbons. Especially preferred is toluene.

The amount of the reaction solvent used in the washing step is usually from 0.3 to 10 times by weight, preferably 1 to 5 times by weight, more preferably 1 to 3 times by weight based on the amount of the acid aqueous solution.

Furthermore, in the case where the distribution rate of the intended acid salt of the oxycarbonyl-substituted piperazine derivative into the water layer declines due to the ingress of the reaction solvent used in the reaction step, if the reaction solvent is distilled away beforehand by such an operation as concentration under reduced pressure or azeotropy, the recovery rate can be enhanced. For example, in the case where the reaction solvent is dissolved in both water and the organic solvent, the acid aqueous solution is concentrated at a concentration temperature of 50 to 100° C. under a reduced pressure of 4 to 100 kPa, for distilling away the reaction solvent, and subsequently the washing solvent is added. The washing step is performed usually in a range from 0 to 80° C., preferably from 10 to 60° C., and more preferably from 20 to 40° C.

After the acid salt is washed using an organic solvent, a usually used base such as sodium hydroxide or potassium hydroxide is used in the obtained water layer, for making the system alkaline internally, and the oxycarbonyl-substituted piperazine derivative is extracted using an organic solvent. It is preferred that the organic solvent used here is 10% or less in the mutual solubility with water at 20° C., considering the recovery rate of the oxycarbonyl-substituted piperazine derivative at the time of extraction. Examples include the organic solvents enumerated for the washing step before. Preferred are aromatic hydrocarbons, and especially preferred is toluene.

In the extraction step, as required, an inorganic salt typified by sodium chloride or sodium sulfate can also be added to salt out the oxycarbonyl-substituted piperazine derivative, for enhancing the recovery rate.

The following concretely describes the distillation step.

It is predicted difficult to remove the impurities represented by the general formula (6) and (7) in the washing step, since they form acid salts like the oxycarbonyl-substituted piperazine derivative represented by the general formula (2) in the acid aqueous solution in the washing step.

Therefore, the piperazine derivatives represented by the general formula (6) and the general formula (7) can be removed by distillation. That is, the piperazine derivative represented by the general formula (6) can be cut as a low-boiling component, and the piperazine derivative represented by the general formula (7) can be cut as a high-boiling component. Furthermore, in the distillation step, the piperazine derivative represented by the general formula (5) and the alcohol represented by the general formula (8) respectively remaining in the washing step without being removed can also be removed as a high-boiling component and a low-boiling component respectively.

The following describes the thermal stability of the oxycarbonyl-substituted piperazine derivative represented by the general formula (2).

We evaluated and analyzed the thermal stability of the oxycarbonyl-substituted piperazine derivative represented by the general formula (2), and as a result, found that the compound is partially thermally decomposed. That is, it was found that the oxycarbonyl group causes decarboxylation owing to heat. It was confirmed that the stability of the compound is greatly affected by the temperature and the heating time period.

The following is a concrete description using 1-benzyloxycarbonyl-3-methylpiperazine as an example.

It was noticed that when, for example, 1-benzyloxycarbonyl-3-methylpiperazine with a purity of 99.3 liquid chromatography area % was allowed to stand at 120° C., 160° C. or 200° C. for 12 hours, their liquid chromatography purity declined to 99.0 liquid chromatography area %, 95.6 liquid chromatography area % and 59.7 liquid chromatography area % respectively, and that the liquid chromatography purity of 1-benzyl-4-benzyloxycarbonyl-2-methylpiperazine corresponding to the compound represented by the general formula (7) rose to 0.2 liquid chromatography area %, 3.2 liquid chromatography area % and 30.7 liquid chromatography area % respectively.

Furthermore, when the compound was allowed to stand at 160° C. for 1 hour, the purity was 98.8 liquid chromatography area %, and it can be seen that the decomposition rate was small compared with the case of 12 hours.

That is, it can be said that the benzyloxycarbonyl-substituted piperazine derivative represented by the general formula (2) is more likely to be decomposed when the heating temperature is higher and when the heating time period is longer.

Therefore, in the distillation step, attention must be paid to the operation conditions such as temperature and time, and it is preferred to carry out the distillation operation with the maximum reduced pressure at a temperature as low as possible with the heating time kept short. Concretely it can be said preferable that the inner temperature of the distiller is 240° C. or lower.

It is preferred that the pressure during distillation is lower, particularly 1.33 to 1330 Pa, preferably 1.33 to 133 Pa.

In the case where distillation is performed, as the equipment, either a batch distiller or a thin film distiller can be used.

In the case of a batch distiller, it is preferred that the supplied amount of the raw material is ½ or less of the entire capacity of the distiller for shortening the heating time. More preferred is ⅓ or less, and further more preferred is ¼ or less. Using such an idea, the heat history time of the distillation raw material can be shortened to lower the thermal decomposition rate.

On the other hand, in the case of a thin film distiller, the raw material feed rate is different depending on the temperature of the thin film portion, internal pressure, the size and specifications of the thin film distiller and the piperazine derivative used. It is preferred to adjust the internal pressure of the distiller, the temperature of the heat source and the raw material feed rate in response to the boiling point of the oxycarbonyl-substituted piperazine derivative, for optimizing the distillation conditions. Particularly in the case where a thin film distiller with a heating surface area of 0.005 to 0.02 m² is used, it is preferred that the internal pressure of the distiller is from 1.33 to 133 Pa and that the raw material feed rate is from 2 to 30 liters/h. More preferred are from 1.33 to 133 Pa and from 5 to 20 liters/h.

Irrespective of the distiller used for distillation, if the raw material contains 1 to 10 wt % of a solvent with a low boiling point, it is preferred to cut the low-boiling solvent at a low temperature, for example, 150° C., for decreasing the solvent content to 2 wt % or less before performing product distillation.

Irrespective of the distiller used, the distillation step can be performed, but it is preferred to use a thin film distiller. On a laboratory scale, the difference between both the distillers does not clearly appear, but in the case where distillation is performed on an industrial scale, it is considered that a thin film distiller is more advantageous. In this case, the distillate in the latter half of distillation is subject to a heat history of longer time. So, in the case of a thin film distiller, since the contact time with the heat source can be kept shortest, the temperature of the heat source can be raised compared with that of a batch distiller, it can be said to be more suitable for distillation of a thermally unstable compound with a high boiling point. Therefore, it can be said that a thin film distiller is suitable for the distillation of the oxycarbonyl-substituted piperazine derivative. If the distillation step is performed, the impurities represented by the general formula (5) and the general formula (8), which could not be removed in the washing step, can be removed.

Therefore, the distillation step exhibits a further higher effect, if it is performed in combination with the washing step.

The following describes the method for measuring the impurities represented by the general formulae (5) to (8) contained in the reaction solution containing the oxycarbonyl-substituted piperazine derivative represented by the general formula (2) and the method for calculating the impurity contents based on the liquid chromatography area percentages.

For measuring the contents of the impurities contained in the oxycarbonyl-substituted piperazine derivative represented by the general formula (2), liquid chromatography is used. The analytical column for liquid chromatography used for analysis is a column using an octadecyl-based composition as a packing material. Particularly the use of Capcellpak C18, 120 angstroms, 5 μm, 4.6 mm×150 mm (Shiseido) is desirable.

The following particularly shows the conditions for analyzing 1-benzyloxycarbonyl-3-methylpiperazine.

The mobile phase is 5 mM sodium dodecyl sulfate (hereinafter abbreviated as SDS) aqueous solution (pH 2.5, phosphoric acid)/acetonitrile, and a gradient method for changing the composition with the lapse of time is used for analysis. That is, the acetonitrile content in the mobile phase is kept at 31 vol % from the start of analysis to 15 minutes later, and the acetonitrile content is then increased at a constant rate up to 45 vol %, taking 10 minutes, being kept at 45 vol % from 25 minutes later to 40 minutes later. The detector used is a UV measuring instrument, and the detection wavelength is 210 nm. The detection wavelength is very important, and if the detection wavelength is changed, the analyzed value may change. The reason is that the maximum wavelength of UV absorption changes depending on the compound. In this system, it is desirable that the wavelength is from 210 to 230 nm at which the ratios of the absorption sensitivity of the compound represented by the general formula (2) to the absorption sensitivities the compounds represented by the general formulae (5) to (8) are from 0.6 to 1.5. Analysis is made at a column oven temperature of 40° C. In the case where analysis is made under the above-mentioned analytical conditions, the retention times of 1-benzyloxycarbonyl-3-methylpiperazine and the impurities corresponding to the general formulae (5) to (8), i.e., 1,4-bis(carbobenzyloxy)-2-methylpiperazine, 1-benzyl-3-methylpiperazine, 4-benzyloxycarbonyl-1-benzyl-2-methylpiperazine and benzyl alcohol were 23.1 minutes, 31.0 minutes, 31.0 minutes, 30.0 minutes and 2.7 minutes respectively. The values of their area percentages can be used to obtain the impurity contents.

The contents of the impurities represented by the general formulae (5) to (8) contained in the reaction solution containing the oxycarbonyl-substituted piperazine derivative can be obtained in reference to the total amount of the impurities represented by the general formula (5) to (8) and the oxycarbonyl-substituted piperazine derivative represented by the general formula (2), i.e., from the following calculation formula $\{A1/(A1+A2+A3+A4+A5)\times100(\%)\}$, wherein A1, A2, A3, A4 and A5 respectively denote the area percentage of the oxycarbonyl-substituted piperazine derivative represented by the general formula (2), the area percentage of the impurity represented by the general formula (5), the area percentage of the impurity represented by the general formula (6), the area percentage of the impurity represented by the general formula (7) and the area percentage of the impurity represented by the general formula (8). Similarly the contents of the respective impurities can be obtained.

As described above, in the case where a piperazine derivative is oxycarbonylated to produce an oxycarbonyl-substituted piperazine derivative, the refining by washing and/or distillation is very useful.

The oxycarbonyl-substituted piperazine derivative obtained as described above is a compound useful, for example, as a raw material of medicines.

The process is described below in detail in reference to examples, but is not limited thereto or thereby. In the following, benzyloxycarbonylation is briefly expressed as Z -protection, and tert-butoxycarbonylation, as Boc-protection.

The analytical conditions for the Z-protection reaction and Boc-protection reaction of 2-methylpiperazine are shown below.

1) Analysis of Z-Protection Reaction Composition

Model: Shimadzu LC-10Vp

Column: Capcellpak C18, 120 angstroms, 5 μm, 4.6 mm×250 mm (Shiseido)

Mobile phase: 5 mM sodium dodecyl sulfate aqueous solution (adjusted to pH 2.5 using phosphoric acid)/$CH_3CN$=69/31 (0-15 min), 55/45 (25-40 min)

Flow rate: 1.0 ml/min

Temperature: 40° C.

Detector: UV (210 nm)

Retention Times:

2.7 min . . . benzyl alcohol {corresponding to general formula (8)}

21.1 min . . . 1-benzyloxycarbonyl-3-methylpiperazine 15.9 min . . . toluene (washing solvent)

30.0 min . . . 1-benzyl-4-benzyloxycarbonyl-2-methylpiperazine 31.0 min . . . 1-benzyl-2-methylpiperazine 31.0 min . . . 1,4-bis(benzyloxycarbonyl)-2-methylpiperazine The reaction yield of 1-benzyloxycarbonyl-3-methylpiperazine by the Z-protection reaction was calculated from the following formula using the internal standard method.

Reaction yield=(1-benzyloxycarbonyl-3-methylpiperazine content in the reaction solution)/(Supplied amount of 2-methylpiperazine)×100(%)

2) Analysis of Boc-Protection Reaction Composition

Model: Shimadzu GC-14B

Column: Neutrabond-1, 60 m×0.25 mm ID, 0.4 μm (GL Science)

Column temperature: 70° C. (10 min)–(+10° C./min)–270° C. (10 min)

Injection temperature: 200° C.

Detection temperature: 200° C.

Detector: FID

Carrier gas: He

Injection port pressure: 200 kg/cm$^2$

Split flow rate: 8 ml/min

Purge flow rate: 40 ml/min

Retention Times:

11.3 min . . . 2-methylpiperazine 24.0 min . . . 1-tert-butoxycarbonyl-3-methylpiperazine 24.1 min . . . 1-tert-butoxycarbonyl-2-methylpiperazine 29.9 min . . . 1,4-bis(tert-butoxycarbonyl)-2-methylpiperazine The conversion and selectivity of 1-tert-butoxycarbonyl-3-methylpiperazine by the Boc -protection reaction were calculated from the following formulae using the GC area value of the peak attributable to 2-methylpiperazine and/or 1-tert-butoxycarbonyl-3-methylpiperazine derivatives on the GC analysis chart.

Conversion - [1-{Area value of 2-methylpiperazine in the reaction solution}/{Area value of 2-methylpiperazine in the reaction solution+Area value of 1-tert-butoxycarbonyl-3-methylpiperazine +Area value of 1-tert-butoxycarbonyl-2-methylpiperazine+Area value of 1,4-bis-(tert-butoxy -carbonyl-2-methylpiperazine)}]×100 (%)

Selectivity=(Area value of 1-tert-butoxycarbonyl-3-methylpiperazine in the reaction solution)/{Area value of 1-tert-butoxycarbonyl-3-methylpiperazine+Area value of 1-tert-butoxy -carbonyl-2-methylpiperazine+Area value of 1,4-bis(tert-butoxycarbonyl-2-methylpiperazine)}×100(%)

Furthermore, the reaction yield of 1-tert-butoxycarbonyl-3-methylpiperazine was calculated from (the conversion×the selectivity)/100(%).

2) Analysis of 2-Methylpiperazine Content

The optically active 2-methylpiperazine in the mother liquor obtained at the time of salt decomposition was determined by the internal standard method using gas chromatography (GC). The analytical conditions were as follows:

Model: Shimadzu GC-14B

Column: Neutrabond-1, 0.25 mm ID×60 m, 0.4 μm (GL Science)

Column temperature: 70° C. (10 min)→(+20° C./min)<270° C. (10 min)

Injection temperature: 230° C.

Detection temperature: 230° C.

Detector: FI)

Carrier gas: He

Injection port pressure: 200 kg/cm$^2$

Split flow rate: 8 ml/min

Purge flow rate: 40 ml/min

Retention Times:

10.2 min . . . 2-methylpiperazine 17.3 min . . . Triglyme (internal standard)

3. Optical Purity Analysis of 2-methylpiperazine

Model: Shimadzu LC-10Vp

Column: Mightysil RP-18 GP, 4.6 mm×150 mm (Kanto Kagaku)

Mobile phase: 0.03 v/v % ammonia aqueous solution (adjusted to pH 4.7 using acetic acid)/$CH_3CN$=65/35 (v/v)

Flow rate: 1.0 ml/min

Temperature: 40° C.

Detector: UV (243 nm)

Pretreatment of Sample

A sample corresponding to about 0.1 g of 1-benzyloxycarbonyl-3-methylpiperazine is placed in a 50 ml measuring flask, and acetonitrile is used for dilution up to the marked line. Then, 0.3 ml of the solution was placed in a 5 ml sample bottle, and 1.5 ml of p,p'-ditoluoyltartaric anhydride (D-PTAN) solution is added, being followed by stirring and subsequent standing in a 50° C. warm bath for 1 hour. Subsequently 0.5 ml of 2% phosphoric acid water is added, being followed by standing for 10 minutes.

4. Optical Purity Analysis of 1-benzyloxycarbonyl-3-methylpiperazine

Model: Shimadzu LC-10Vp

Column: Mightysil RP-18 GP, 4.6 mm×150 mm (Kanto Kagaku)

Mobile phase: 0.03 v/v % ammonia aqueous solution (adjusted to pH 4.7 using acetic acid)/$CH_3CN$=67/33 (v/v)

Flow rate: 1.0 ml/min

Temperature: 40° C.

Detector: UV (243 nm)

Pretreatment of Sample

A sample corresponding to about 0.1 g of 1-benzyloxycarbonyl-3-methylpiperazine is placed in a 50 ml measuring flask, and acetonitrile is used for dilution up to the marked line. Then, 0.3 ml of the solution is placed in a 5 ml sample bottle, and 1.5 ml of p,p'-ditoluoyltartaric anhydride (D-PTAN) solution is added, being followed by stirring and subsequent standing in a 70° C. warm bath for 1 hour. Subsequently 0.5 ml of 2% phosphoric acid water is added, being followed by standing for 10 minutes.

The product content and the main byproduct contents of the reaction solution and the optical purity of the product were analyzed by means of liquid chromatography respectively under different analytical conditions. The optical purity was calculated using the area values of R-isomer peak and S-isomer peak. In the case where S-isomer was selectively produced, calculation from the following formula was made.

Optical purity (% ee)={(Area value of S-isomer peak–Area value of R-isomer peak)/(Area value of S-isomer peak+Area value of R-isomer peak)}×100(%)

The water content of the organic solvent was measured using a Karl Fischer water content meter.

The following exemplifies the synthesis of 1-benzyloxy-3-methylpiperazine and 1-tert-butoxycarbonyl-3-methylpiperazine by the Z-protection reaction and Boc-protection reaction of 2-methylpiperazine.

EXAMPLE 1

In a 100 ml four-neck flask, 5.00 g (=0.0499 mole) of racemic 2-methylpiperazine was placed, and 44 g of 1-butanol (water content 0.05 wt %) was added for dissolution. The solution was cooled to 0° C., and 8.47 g of benzyl chlorocarbonate (=0.0489 mole, purity by HPLC determination analysis 98.5 wt %, 0.98 molar time) was added dropwise in a liquid temperature range from 0 to 8° C. Then, stirring was carried out at 0 to 5° C. for 2 hours, and the reaction solution was partially sampled and determined by the internal standard method (internal standard: anisole). As a result, the reaction yield of 1-benzyloxycarbonyl-3-methylpiperazine was 83.9% (based on the amount of 2-methylpiperazine). The reaction solution was further stirred at room temperature for 12 hours and analyzed. As a result, the reaction yield was 85.1%.

EXAMPLE 2

A reaction was performed as described for Example 1, except that the amount of benzyl chlorocarbonate used was changed from 8.45 g to 9.25 g (=0.0533 mole, 1.07 molar times). As a result, the reaction yield of 1-benzyloxycarbonyl-3-methylpiperazine was 91.7% (based on the amount of 2-methylpiperazine) after lapse of 2 hours at 0 to 5° C. Furthermore, the reaction solution was stirred at room temperature for further 12 hours and analyzed. As a result, the reaction yield was 94.5%.

From the obtained reaction solution, 1-butanol was distilled away, and 30 g of water was added to the concentrate. The pH was adjusted to 11.2 using 48% sodium hydroxide. To the solution, 40 g of toluene was added, and the lower layer was removed. Subsequently, the upper layer was concentrated under reduced pressure to distill away toluene, for obtaining 11.1 g of a recovered solution.

The obtained recovered solution was analyzed, and as a result, the intended 1-bunzyloxycarbonyl-3-methylpiperazine occupied 87.2 area %, and as for impurities, benzyl alcohol occupied 0.52 area %, 1-benzyl-4-benzyloxycarbonyl-2-methylpiperazine, 0.01 area %, 1-benzyl-2-methylpiperazine, 0.10 area %, and 1,4-dibenzyloxycarbonyl-2-methylpiperazine, 11.9 area % (solvent toluene, 1.9 area %). Therefore, the total of impurities was 6 liquid chromatography area %.

EXAMPLE 3

A reaction was performed as described for Example 1, except that the amount of benzyl chlorocarbonate used was changed from 8.47 g to 10.1 g (=0.0597 mole, 1.17 molar times). As a result, the reaction yield of 1-benzyloxycarbonyl-3-methylpiperazine was 93.8% (based on the amount of 2-methylpiperazine) after lapse of 2 hours at 0 to 5° C. Stirring was carried out at room temperature for further 12 hours, being followed by analysis. As a result, the reaction yield was 95.1%.

EXAMPLE 4

A 1-liter four-neck flask with a thermometer, condenser and stirrer was charged with 100.2 g (=1.00 mole) of 2-methylpiperazine provided as a racemic modification, 90.0 g (=0.600 mole) of D-tartaric acid, 170 g of water and 36.0 g (=0.600 mole) of acetic acid, being followed by heating up to 72° C. and aging at the temperature for 2 hours. The amount of the solvent based on the amount of racemic 2-methylpiperazine was 1.69 times by weight. Then, cooling was carried out down to 15° C., taking 12 hours, and precipitated crystals were collected by filtration.

The obtained crystals were dried in vacuum, to obtain 114.0 g (=0.456 mole) of a diastereomer salt. The optical purity of the salt was 93.25% ee, and the S-isomer yield in the obtained salt based on the amount of the S-isomer in the 2-methylpiperazine supplied as a racemic modification was 88.0%.

Then, a 500 ml flask was charged with 190 g of water, and 114.0 g of the obtained crystals {pure (S)-2-methylpiperazien content=44.0 g} were added. Perfect dissolution was achieved at 80 to 85° C., being followed by cooling down to 15° C., taking 5 hours. Precipitated crystals were collected by filtration and dried in vacuum, to obtain 100.5 g of a salt. Its optical purity was 99.5% ee, and the S-isomer yield in the obtained salt based on the amount of the (S)-2-methylpiperazine in the supplied crystals was 91.1%.

A 200 ml four-neck flask with a thermometer, condenser and stirrer was charged with 75 g of water, and 25.1 g of (S)-2-methylpiperazine D-tartaric acid salt (=0.100 mole, optical purity of 2-methylpiperazine=99.5% ee) and 7.8 g (=0.100 mole) of 95% pure calcium hydroxide were added. The slurry was heated up to 70 to 80° C., and stirred for 3 hours, then being cooled to room temperature. Then, the non-dissolved solvent was filtered away to obtain the mother liquor. The mother liquor was GC-analyzed, and as a result, it was found that 9.2 g (=0.0918 mole) of 2-methylpiperazine existed in the mother liquor (yield 91.8%). Furthermore, from the result of HPLC analysis, the optical purity of (S)-2-methylpiperazine was 99.5% ee.

Subsequently concentration was carried out down to a water content of about 50 wt %, and 1-butanol was added. Then, azeotropic dehydration was carried out till the water content of the system became less than 1 wt %, and distillation under reduced pressure was carried out to isolate (S)-2-methylpiperazine.

The optically active (S)-2-methylpiperazine (optical purity 99.5% ee) obtained as described above was used to perform a reaction in quite the same way as the method of Example 1. Stirring was carried out for 2 hours at 0 to 5° C., being followed by stirring at room temperature for 12 hours. The reaction solution was analyzed, and as a result, the reaction yield of 1-benzyloxycarbonyl-3-methylpiperazine was 84.6% (based on the amount of 2-methylpiperazine), and its optical purity was 99.5% ee, showing no decline of optical purity.

EXAMPLE 5

A reaction was carried out as described for Example 1, except that the solvent was changed from 44 g of 1-butanol to a mixed solvent consisting of 5.3 g of water and 40 g of 1-butanol (water content 10.6 wt %). After stirring at 0 to 5° C. for 2 hours, the reaction solution was analyzed. As a result, the reaction yield of 1-benzyloxycarbonyl-3-methylpiperazine was 82.1% (based on the amount of 2-methylpiperazine).

COMPARATIVE EXAMPLE 1

A reaction was carried out as described for Example 1, except that the solvent was changed from 44 g of 1-butanol to a mixed solvent consisting of 9 g of water and 35 g of 1-butanol (water content 20.5 wt %). After stirring at 0 to 5° C. for 2 hours, the reaction solution was analyzed. As a result, the reaction yield of 1-benzyloxycarbonyl-3-methylpiperazine was 59.6% (based on the amount of 2-methylpiperazine).

COMPARATIVE EXAMPLE 2

A reaction was carried out as described for Example 4, except that the solvent was changed from 44 g of 1-butanol to a mixed solvent consisting of 18 g of water and 27 g of 1-butanol (water content 40.0 wt %). After stirring at 0° C. for 2 hours, the reaction solution was analyzed. As a result, the reaction yield of 1-benzyloxycarbonyl-3-methylpiperazine was 51.6% (based on the amount of 2-methylpiperazine).

COMPARATIVE EXAMPLE 3

A reaction was carried out as described for Example 1, except that the solvent was changed from 44 g of 1-butanol to a mixed solvent consisting of 22 g of water and 22 g of 1-butanol (water content 50 wt %). After stirring at 0° C. for 2 hours, the reaction solution was analyzed. As a result, the reaction yield of 1-benzyloxycarbonyl-3-methylpiperazine was 33.6% (based on the amount of 2-methylpiperazine).

COMPARATIVE EXAMPLE 4

A 200 ml four-neck flask with a pH meter and dropping funnel was charged with10.02 g (=0.100 mole) of racemic 2-methylpiperazine, and 50.0 g of 1-butanol was added for dissolution, being followed by addition of 50.1 g of water (water content 50.0 wt %). With vigorous stirring, benzyl chlorocarbonate was added dropwise. In this case, 48 wt % sodium hydroxide aqueous solution was added dropwise to keep the pH value of the system at 10 to 11, and as required, the system was cooled with ice to keep the internal temperature at 23 to 26° C. (final water content 52.1 wt %). After completion of dropwise addition, with vigorous stirring, aging was carried out for 2 hours. The reaction solution was sampled and analyzed, and as a result, the reaction yield of 1-benzyloxycarbonyl-3-methylpiperazine was 40.1%.

COMPARATIVE EXAMPLE 5

A 200 ml four-neck flask with a pH meter and dropping funnel was charged with 10.02 g (=0.100 mole) of racemic 2-methylpiperazine, and 80.2 g of 1-butanol was added for dissolution, being followed by addition of 20.1 g of water (water content 20.0 wt %). With vigorous stirring, benzyl chlorocarbonate was added dropwise. In this case, 48 wt % sodium hydroxide aqueous solution was added dropwise to keep the pH value of the system at 7.5 to 8.5, and as required, the system was cooled with ice to keep the internal temperature at 23 to 26 (final water content 23.0 wt %). After completion of dropwise addition, with vigorous stirring, aging was carried out for 2 hours. The reaction solution was sampled and analyzed, and as a result, the reaction yield of 1-benzyloxycarbonyl-3-methylpiperazine was 50.4%.

EXAMPLE 6

A reaction was carried out as described for Example 1, except that the solvent was changed from 44 g of 1-butanol to 44 g of ethanol (water content 0.06 wt %). After stirring at 0° C. for 2 hours, the reaction solution was analyzed. As a result, the reaction yield of 1-benzyloxycarbonyl-3-methylpiperazine was 83.4% (based on the amount of 2-methylpiperazine).

COMPARATIVE EXAMPLE 6

A reaction was carried out as described for Example 6, except that the solvent was changed from 44 g of ethanol to a mixed solvent consisting of 22 g of water and 22 g of ethanol (water content 50.0 wt %). As a result, the reaction yield of 1-benzyloxycarbonyl-3-methylpiperazine was 37.7% (based on the amount of 2-methylpiperazine).

EXAMPLE 7

A reaction was carried out as described for Example 1, except that 12.5 g of (S) -2-methylpiperazine D-tartaric acid salt (5.0 g=0.0499 mole as 2-methylpiperazine) was used instead of 5.0 g (=0.0499 mole) of 2-methylpiperazine) and that the amount of benzyl chlorocarbonate used was changed from 8.47 g to 8.90 g (=0.0514 mole). However, after reaction at 0° C. for 2 hours, aging was carried out at 25° C. for 12 hours. As a result, the reaction yield of 1-benzyloxycarbonyl-3-methylpiperazine was 85.9% (based on the amount of 2-methylpiperazine).

COMPARATIVE EXAMPLE 7

A reaction was carried out as described for Example 7, except that the solvent was changed from 44 g of 1-butanol to 26 g of 1-butanol and 18 g of water (water content 40.9 wt %). As a result, the reaction yield of 1-benzyloxycarbonyl-3-methylpiperazine was 51.6% (based on the amount of 2-methylpiperazine).

EXAMPLE 8

In a 100 ml four-neck flask, 5.04 g (=0.0503 mole) of racemic 2-methylpiperazine was placed, and 5.37 g of water and 45.13 g of 1-butanol were added for dissolution (water content 10.6 wt %). Furthermore, 3.99 g (=0.0504 mole) of pyridine was added, being followed by stirring and subsequent cooling down to 0° C., and 8.67 g of benzyl chlorocarbonate (=0.0494 mole, purity by HPLC determination analysis 97.1 wt %, 0.98 molar time) was added dropwise with the liquid temperature kept in a range from 5 to 10° C. Then, stirring was carried out at 0° C. for 2 hours. The reaction solution was analyzed, and as a result, the reaction yield of 1-benzyloxycarbonyl-3-methylpiperazine was 82.5%.

EXAMPLE 9

In a 100 ml four-neck flask, 5.06 g (=0.0505 mole) of racemic 2-methylpiperazine was placed, and 50.00 g of 1-butanol (water content 0.05 wt %) was added for dissolution. After cooling down to 0° C., 10.91 g (=0.0500 mole, 0.99 molar time) of di-tert-butyl dicarbonate was added dropwise with the liquid temperature kept in a range from 5 to 15° C. Then, stirring was carried out at 5 to 10° C. for 2 hours. The reaction solution was analyzed, and as a result, the conversion of 2-methylpiperazine was 94.7%, while the selectivity of 1-tertbutoxycarbonyl-3-methylpiperazine was 89.3% (reaction yield 84.6%).

EXAMPLE 10

An experiment was carried out as described for Example 9, except that the amount of di-tert-butyl dicarbonate used was changed to 11.97 g (=0.0548 mole, 1.10 molar times). As a result, the conversion of 2-methylpiperazine was 100.0%, and the selectivity of 1-tert-butoxycarbonyl-3-methylpiperazine was 81.5% (reaction yield 81.5%).

EXAMPLE 11

An experiment was carried out as described for Example 9, except that 45.55 g of 1-butanol and 4.61 g of water (water content 9.2 wt %) were used instead of 50.00 g of 1-butanol. As a result, the conversion of 2-methylpiperazine was 94.3%, and the selectivity of 1-tert-butoxycarbonyl-3-methylpiperazine was 85.8% (reaction yield 80.9%).

COMPARATIVE EXAMPLE 8

An experiment was carried out as described for Example 9, except that 37.56 g of 1-butanol and 12.67 g of water (water content 25.2 wt %) were used instead of 50.00 g of 1-butanol. As a result, the conversion of 2-methylpiperazine was 81.6%, and the selectivity of 1-tert-butoxycarbonyl-3-methylpiperazine was 70.9% (reaction yield 57.9%).

COMPARATIVE EXAMPLE 9

An experiment was carried out as described for Example 9, except that 25.00 g of 1-butanol and 25.00 g of water (water content 50.0 wt %) were used instead of 50.00 g of 1-butanol. As a result, the conversion of 2-methylpiperazine was 81.2%, and the selectivity of 1-tert-butoxycarbonyl-3-methylpiperazine was 41.8% (reaction yield 33.9%).

COMPARATIVE EXAMPLE 10

A 200 ml four-neck flask with a pH meter and dropping funnel was charged with 10.08 g (=0.101 mole) of racemic 2-methylpiperazine, and 50.0 g of 1-butanol was added for dissolution, being followed by addition of 50.3 g of water (water content 50.1 wt %). With vigorous stirring, benzyl chlorocarbonate was added dropwise. In this case, 48 wt % sodium hydroxide aqueous solution was added dropwise to keep the pH value of the system at 10 to 11, and as required, the system was cooled with ice to keep the internal temperature at 23 to 26° C. (final water content 53.2 wt %). After completion of dropwise addition, with vigorous stirring, aging was carried out for 2.5 hours. The reaction solution was sampled and analyzed, and as a result, the conversion of 2-methylpiperazine was 85.5%, and the selectivity of 1-tert-butoxycarbonyl-3-methylpiperazine was 77.2% (reaction yield 66.0%).

COMPARATIVE EXAMPLE 11

A 200 ml four-neck flask with a pH meter and dropping funnel was charged with 10.22 g (=0.102 mole) of racemic 2-methylpiperazine, and 80.5 g of 1-butanol was added for dissolution, being followed by addition of 27.5 g of water (water content 25.4 wt %). With vigorous stirring, benzyl chlorocarbonate was added dropwise. In this case, 48 wt % sodium hydroxide aqueous solution was added dropwise to keep the pH value of the system at 8 to 9.5, and as required, the system was cooled with ice to keep the internal temperature at 23 to 26 (final water content 26.9 wt %). After completion of dropwise addition, with vigorous stirring, aging was carried out for 2.5 hours. The reaction solution was sampled and analyzed, and as a result, the conversion of 2-methylpiperazine was 89.6%, and the selectivity of 1-tert-butoxycarbonyl-3-methylpiperazine was 73.5% (reaction yield 65.9%).

EXAMPLE 12

The reaction solution obtained by the same operation as in Example 2 was concentrated and 31 g of 1-butanol was distilled away under reduced pressure, being followed by addition of 30 g of water. Subsequently 35% hydrochloric acid water was used for adjusting the pH to 0.8. Then, 22 g of toluene was added, and stirring was carried out for 30 minutes. The upper layer was then removed, and the same amount of toluene was added again. The same operation was repeated for carrying out washing operation. Subsequently 48% sodium hydroxide aqueous solution was used to keep the pH of the reaction solution at 11.5. In this case, white turbidity occurred due to liberated 1-benzyloxycarbonyl-3-methylpiperazine. To the white turbid solution, 40 g of toluene was added, and stirring was carried out for 30 minutes. The lower layer was then removed, and the upper layer was concentrated under reduced pressure at 60 to 70° C. in temperature. Then, toluene was distilled away to obtain 10.13 g of 1-benzyloxycarbonyl-3-methylpiperazine.

The obtained compound was analyzed. As a result, the intended 1-benzyloxycarbonyl-3-methylpiperazine accounted for 98.0 liquid chromatography area %. The impurities showed 0.40 liquid chromatography area % for benzyl alcohol, 0.04 liquid chromatography area % for 1-benzyl-4-benzyloxycarbonyl-2-methylpiperazine, 0.10 liquid chromatography area % for 1-benzyl-2-methylpiperazine and no detection for 1,4-dibenzyl-oxycarbonyl-2-methylpiperazine (1.46 liquid chromatography area % for solvent toluene). Therefore, the total of impurities was 0.55 liquid chromatography area %.

EXAMPLE 13

The reaction solution obtained by the same operation as in Example 2 was concentrated and 28 g of 1-butanol was distilled away under reduced pressure, being followed by addition of 30 g of water. Subsequently 35% hydrochloric acid water was used for adjusting the pH to 0.7. Then, 22 g of toluene was added, and stirring was carried out for 30 minutes. The upper layer was then removed, and the same amount of toluene was added again. The same operation was repeated for carrying out washing operation. Subsequently 48% sodium hydroxide aqueous solution was used to keep the pH of the reaction solution at 11.8. In this case, white turbidity occurred due to liberated 1-benzyloxycarbonyl-3-methylpiperazine. To the white turbid solution, 40 g of toluene was added, and stirring was carried out for 30 minutes. The lower layer was then removed, and the upper layer was concentrated under reduced pressure at 60 to 70° C. in temperature. Then, toluene was distilled away.

Ten point three two grams of the obtained 1-benzyloxycarbonyl-3-methylpiperazine was placed in a 10 ml heart flask and distilled in vacuum. When the oil bath reached 145° C., the removal by distillation started, and the temperature was raised finally up to 170° C. The internal pressure ranged from 40 to 53 Pa, and the temperature at the column top ranged from 131 to 140° C.

The obtained compound was analyzed. As a result, the intended 1-benzyloxycarbonyl-3-methylpiperazine accounted for 99.7 liquid chromatography area %. The impurities showed 0.03 liquid chromatography area % for benzyl alcohol, 0.18 liquid chromatography area % for 1-benzyl-4-benzyloxycarbonyl-2-methylpiperazine, 0.04 liquid chromatography area % for 1-benzyl-2-methylpiperazine and no detection for 1,4-dibenzyloxycarbonyl-2-methylpiperazine (for solvent toluene either). Therefore, the total of impurities was 0.25 liquid chromatography area %.

EXAMPLE 14

A 1-liter four-neck flask with a thermometer, condenser and stirrer was charged with 100.2 g (=1.00 mole) of 2-methylpiperazine provided as a racemic modification, 90.0 g (=0.600 mole) of D-tartaric acid, 170 g of water and 48.0 g (=0.800 mole) of acetic acid, and the temperature was raised up to 72° C., being followed by aging at the temperature for 2 hours. The amount of the solvent based on the amount of 2-methylpiperazine provided as a racemic modification was 1.70 times by weight. Then, cooling was carried out down to 15° C., taking 12 hours, and precipitated crystals were collected by filtration.

The obtained crystals were dried in vacuum, to obtain 112.4 g (=0.449 mole) of a diastereomer salt. The optical purity of the salt was 94.4% ee, and the yield of the S-isomer in the obtained salt based on the amount of the S-isomer in the 2-methylpiperazine provided as a racemic modification was 87.3%.

Then, a 500 ml flask was charged with 190 g of water, and 112.4 g of the obtained crystals {pure (S)-2-methylpiperazine content=43.7 g} were added. Perfect dissolution was achieved at 80 to 85° C., and cooling was carried out down to 15° C., taking 12 hours. Precipitated crystals were collected by filtration and dried in vacuum to obtain 99.1 g of a salt. Its optical purity was 99.4% ee, and the yield of the S-isomer in the obtained salt based on the amount of (S)-2-methylpiperazine in the supplied crystals was 90.5%.

A 1-liter four-neck flask with a thermometer, condenser and stirrer was charged with 300 g of water, and 98.3 g of the previously obtained salt of (S)-2-methylpiperazine and D-tartaric acid {pure (S)-2-methylpiperazine content=39.2 g=0.391 mole, optical purity of 2-methylpiperazine=99.4% ee} and 39.6 g (=0.508 mole) of 95% pure calcium hydroxide were added into the flask. The slurry was stirred in a range from 80 to 82° C. for 3 hours, and cooled to room temperature. Then, the non-dissolved salt (calcium tartarate) was filtered away, to obtain the mother liquor.

The mother liquor was GC-analyzed, and as a result, it was found that 39.1 g (=0.390 mole) of optically active 2-methylpiperazine existed in the mother liquor (yield 99.8%). Furthermore, as a result of HPLC analysis, the optical purity of (S)-2-methylpiperazine was 99.4% ee.

Then, concentration was carried out to a water content of about 50 wt %, and 1-butanol was added, and azeotropic dehydration was carried out till the water content of the system became less than 1 wt %.

In a 100 ml four-neck flask, 5.0 g of the obtained (S)-2-methylpiperazine (=0.0499 mole, optical purity 99.4% ee) was placed, and 44 g of 1-butanol was added for dissolution. The solution was cooled down to 0° C., and 9.25 g (=0.0534 mole) of benzyl chlorocarbonate was added dropwise with the liquid temperature kept in a range from 0 to 8° C.

Then, stirring was carried out at 0° C. for 2 hours, and 30 g of 1-butanol was distilled away under reduced pressure. Subsequently 30 g of water was added, and 35% hydrochloric acid water was used to adjust the pH to 1.0. Then, 22 g of toluene was added, and stirring was carried out for 30 minutes. Subsequently the upper layer was removed, and the same amount of toluene was added again. The same operated was repeated to carry out washing operation. Then, 48% sodium hydroxide aqueous solution was used to adjust the pH of the reaction solution to 11.8. In this case, white turbidity occurred due to the liberated 1-benzyloxycarbonyl-3-methylpiperazine. To the white turbid solution, 40 g of toluene was added, and stirring was carried out for 30 minutes. The lower layer was then removed, and the upper layer was concentrated under reduced pressure at 60 to 70° C. in temperature, toluene being then distilled away.

Ten point three two grams of the obtained 1-benzyloxycarbonyl-3-methylpiperazine was placed in a 10 ml heart flask and distilled in vacuum. When the oil bath reached 145° C., the removal by distillation started, and the temperature was raised finally up to 170° C. The internal pressure ranged from 40 to 53 Pa, and the temperature at the column top ranged from 131 to 140° C.

The obtained compound was analyzed. As a result, the intended 1-benzyloxycarbonyl-3-methylpiperazine accounted for 99.7 area %. The impurities showed 0.03 area % for benzyl alcohol, 0.12 for 1-benzyl-4-benzyloxycarbonyl-2-methylpiperazine, 0.08 area% for 1-benzyl-2-methylpiperazine and no detection for 1,4-dibenzyloxycarbonyl-2-methylpiperazine(for solvent toluene either). Therefore, the total of impurities was 0.23 area %. Furthermore, the optical purity was 99.4% ee.

EXAMPLE 15

A 2-liter four-neck flask with a thermometer, condenser and stirrer was charged with 200.4 g (=2.00 moles) of racemic 2-methylpiperazine, 280.0 g of water and 96.0 g of methanol for perfect dissolution. Then, 300.4 g of 50 wt % D-tartaric acid aqueous solution (150.2 g=1.000 mole of D-tartaric acid) was added at 40 to 45° C., and the temperature was further raised up to 72° C., being followed by addition of 120.2 g (=2.00 moles) of acetic acid and aging at the temperature for 2 hours. The solvent composition was water/methanol=81.8/18.2 (ratio by weight), and the amount of the solvent based on the racemic 2-methylpiperazine was 2.63 times by weight. Then, cooling was carried out down to 25° C., taking 12 hours, and precipitated crystals were collected by filtration. The obtained crystals were dried in vacuum, to obtain 214.8 g (=0.858 mole) of a diastereomer salt. The optical purity of the salt was 93.9% ee, and the yield of the S-isomer in the obtained salt based on the amount of the S-isomer in the supplied (+) -2-methylpiperazine was 83.2%.

Subsequently, a 1-liter flask was charged with 380 g of water, and the obtained 214.8 g of crystals {pure (S)-2-methylpiperazine content=83.4 g} were added. Perfect dissolution was achieved at 80 to 85° C., and cooling was carried out down to 15° C., taking 12 hours. Precipitated crystals were collected by filtration and dried in vacuum to obtain 187.2 g of a salt. Its optical purity was 99.4% ee, and the yield of the S-isomer in the obtained salt based on the amount of (S)-2-methylpiperazine in the supplied crystals was 89.8%.

A 500 ml four-neck flask with a thermometer, condenser and stirrer was charged with 150 g of water, and 185.0 g of (S)-2-methylpiperazine D-tartaric acid salt (=0.739 mole, optical purity of 2-methylpiperazine=99.4% ee) obtained before and 69.1 g (=0.863 mole) of 95% pure calcium hydroxide were added. The slurry was heated up to 70 to 80° C., and stirred for 3 hours, then being cooled to room temperature. Subsequently, the non-dissolved salt was filtered away, to obtain the mother liquor. The mother liquor was GC-analyzed, and as a result, it was found that 68.7 g (=0.686 mole) of optically active 2-methylpiperazine existed in the mother liquor (yield 92.8%). Furthermore, as a result of HPLC analysis, the optical purity of (S)-2-methylpiperazine was 99.4% ee.

Then, water was distilled away till about 50 wt % was reached, being followed by addition of 1-butanol, and azeotropic dehydration was carried out till the water content of the system became less than 1 wt %.

In a 1-liter four-neck flask, 50.0 g of the (S)-2-methylpiperazine (=0.499 mole, optical purity 99.4% ee) obtained before was placed, and 440 g of 1-butanol was added for dissolution. The solution was cooled down to 0° C., and 92.5 g (=0.534 mole) of benzyl chlorocarbonate was added dropwise with the liquid temperature kept in a range from 0 to 8° C.

Then, stirring was carried out at 0° C. for 2 hours, and 300 g of 1-butanol was distilled away under reduced pressure, being followed by addition of 300 g of water. Subsequently 35% hydrochloric acid water was used to adjust the pH to 1.0, and 220 g of toluene was added, being followed by stirring for 30 minutes. The upper layer was then removed, and the same amount of toluene was added again. The same operation was repeated to carry out washing operation. Subsequently 48% sodium hydroxide aqueous solution was used to adjust the pH of the reaction solution to 12.1. In this case, white turbidity occurred due to liberated 1-benzyloxycarbonyl-3-methylpiperazine. To the white turbid solution, 400 g of toluene was added, and stirring water carried out for 30 minutes. The lower layer was then removed, and the upper layer was concentrated under reduced pressure at 60 to 70° C. in temperature. Subsequently toluene was distilled away to obtain 88.5 g of a concentrate.

Eighty five point zero grams of the obtained 1-benzyoxycarbonyl-3-methylpiperazine was fed to a thin film distiller (heating surface area 0.02 m$^2$) using a liquid feed pump at 0.6 liter/h. The temperature of the heating medium was 150° C., and a low-boiling component was cut at a vacuum degree of 360 Pa, to obtain 82.8 g of a liquid remaining in the distiller.

The liquid remaining in the distiller was again fed to the same thin film distiller at 0.6 liter/h using a liquid feed pump. The temperature of the heating medium was 220° C., and product distillation was carried out at 87 to 116 Pa in vacuum degree, to obtain 76.1 g of a distillate.

The obtained compound was analyzed. As a result, the intended 1-benzyloxycarbonyl-3-methylpiperazine accounted for 99.4 liquid chromatography area %. The impurities showed 0.25 liquid chromatography area % for benzyl alcohol, 0.03 liquid chromatography area % for 1-benzyl-4-benzyloxycarbonyl-2-methylpiperazine, 0.02 liquid chromatography area % for 1-benzyl-2-methylpiperazine and no detection for 1,4-dibenzyloxycarbonyl-2-methylpiperazine (and 0.08 area % for solvent toluene). Therefore, the total of impurities was 0.30 liquid chromatography area %. Furthermore, the optical purity was 99.4% ee.

EXAMPLE 16

A 1-liter four-neck flask with a thermometer, stirrer and condenser was charged with 100.0 g of water and 90.0 g (=0.600 mole) of D-tartaric acid, and after a homogeneous solution was formed, 200.4 g of an aqueous solution containing 50 wt % of racemic 2-methylpiperazine (pure 2-methylpiperazine content=1.00 mole) and 36.0 g (=0.600 mole) of acetic acid were added at room temperature. A homogeneous solution was formed at 70 to 75° C., and seed crystals were added at 65° C., being followed by aging for 1 hour. Then, cooling was carried out down to 15° C., taking 5 hours, being followed by aging at the temperature for 1 hour. The obtained slurry was separated into a solid and a liquid, to obtain 172.1 g of a wet cake (pure 2-methylpiperazine content=44.78 g=0.447 mole) (optical purity=92.6% ee, S-isomer yield=86.1% based on the amount of supplied S-isomer).

Then, a 1-liter four-neck flask with a thermometer, stirrer and condenser was charged with 130.0 g of water, and 154.9 g of the obtained cake (pure 2-methylpiperazine content=40.30 g=0.402 mole) was added at room temperature. The temperature was raised up to 75 to 85° C. for dissolution, and seed crystals were added at 70° C., being followed by aging for 1 hour, cooling down to 15° C. taking 5 hours and aging at the temperature for 1 hour. The obtained slurry was separated into a solid and a liquid, to obtain 107.0 g of a wet cake (pure 2-methylpiperazine content=36.40 g=0.363 mole) (optical purity=99.5% ee, S-isomer yield=90.3% based on the amount of supplied S-isomer).

Then, a 1-liter four-neck flask with a thermometer, stirrer and condenser was charged with 300 g of water, and 100.0 g of the obtained wet cake (pure 2-methylpiperazine content=34.01 g=0.340 mole) was added. The temperature was raised up to 70° C. for dissolution, and 34.42 g (0.442 mole, 1.3 molar times) of 95% calcium hydroxide was added. Aging was carried out at 78 to 82° C. for 3 hours, and solid-liquid separation was carried out to recover (S)-2-methylpiperazine. The 2-methylpiperazine content in the mother liquor was 33.38 g (=0.333 mole) (recovery rate 98.0%).

From the obtained mother liquor, 230 g of water was distilled away, and 340 g of 1-butanol was added, concentration then being carried out at 60 to 70° C. In this case, Dean and Stark was installed to return the upper layer of the distillate into the distiller. When the water content in the distiller became 2.1 wt %, concentration was stopped, being followed by cooling down to 0° C. The 2-methylpiperazine content of the solution in the distiller was 32.38 g (=0.323 mole) (recovery rate=97.0%).

To the solution, 58.72 g (=0.339 mole, 1.05 molar times) of benzyl chlorocarbonate was added dropwise while the dropwise added amount was adjusted to keep the temperature in the distiller at 0 to 10° C. Then, the temperature was raised to room temperature, being followed by aging for 2 hours, and concentration under reduced pressure was carried out at 60 to 70° C. for distilling away 180 g (pure ZMP content=68.50 g=0.292 mole, reaction yield 90.5%).

Three hundred and eighty grams of toluene was added, and concentration under reduced pressure was carried out at 60 to 70° C., for distilling away 340 g. To the concentrate, 200 g of water was added, and 35% hydrochloric acid water was used to adjust the pH to 1.2. Aging was carried out for 30 minutes, and the upper layer was removed. The same operation was repeated further twice, and 48% sodium hydroxide aqueous solution was used to adjust the pH of the reaction solution to 12.0, being followed by addition of 140 g of toluene and stirring for 30 minutes. The lower layer was then removed, and 100 g of water was added, being followed by stirring. The lower layer was then removed, and the upper layer was concentrated under reduced pressure at 60 to 70° C., toluene being then distilled away at 1.3 kPa and 80° C., to obtain 67.60 g of a concentrate.

The obtained compound was analyzed. As a result, the intended 1-benzyloxycarbonyl-3-methylpiperazine accounted for 97.2 liquid chromatography area %. The impurities showed 0.27 liquid chromatography area % for benzyl alcohol, 0.02 liquid chromatography area % for 1-benzyl-4-benzyloxycarbonyl-2-methylpiperazine, 0.01 liquid chromatography area % for 1-benzyl-2-methylpiperazine and no detection for 1,4-dibenzyloxycarbonyl-2-methylpiperazine (2.44 liquid chromatography area % for solvent toluene). Therefore, the total of impurities was 0.31 liquid chromatography area %.

INDUSTRIAL APPLICABILITY

An oxycarbonyl-substituted piperazine derivative can be produced at a high yield by oxycarbonylating a piperazine derivative under mild conditions using simple equipment.

The invention claimed is:

1. A process for producing an oxycarbonyl-substituted piperazine derivative comprising oxycarbonylating a piperazine derivative represented by formula (1) in the presence of 1) a reagent comprising benzyl chlorocarbonate or di-tert-butyl dicarbonate and an organic alcohol solvent with a water content of 15 wt % or less to produce an oxycarbonyl-substituted piperazine derivative represented by formula (2)

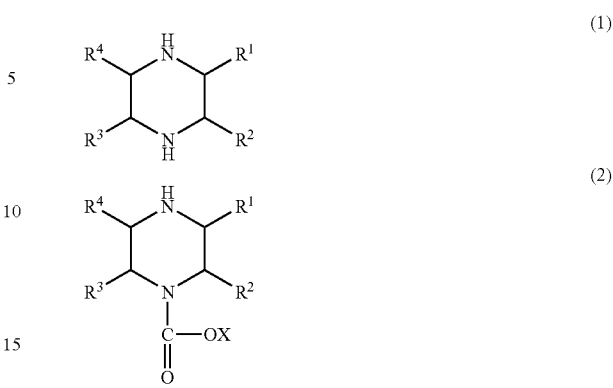

wherein the $R^1$ in the formula (1) and the formula (2) denotes a methyl group, and $R^2$, $R^3$ and $R^4$ denote a hydrogen atom respectively; X denotes a tert-butyl group or benzyl group; and the compounds represented by the formula (1) and the formula (2) are optically active substances, and 2) at least one compound selected from the group consisting of pyridine, α-picoline, β-picoline, γ-picoline, 2-ethylpyridine, 3-ethylpyridine, 4-ethylpyridine, 2-n-propylpyridine, 3-n-propylpyridine, 4-n-propylpyridine, 2-isopropylpyridine, 2-phenylpyridine, 2-vinylpyridine, 3-aminopyridine, 2-hydroxypyridine, 2-methoxypyridine, 2-chloropyrodine, 3-fluoropyridine, 4-bromopyridine, 3-iodopyridine, 2-formylpyridine, 3-acetylpyridine, 2-pyridinecarboxylic acid, methyl 3-pyridinecarboxylate, 3-pyridinecarboxylic acid amide, 2-cyanopyridine, 3-nitropyridine, pyrrole, indole, pyrazole, isoxazole, isothiazole, indazole, imidazole, oxazole, thiazole, benzimidazole, quinoline, isoquinoline, pyridazine, pyrimidine, pyrazine, quinoxaline, carbazole, α-aminonaphthalene, β-aminonaphthalene, aniline, 2.6-lutidine and trimethylamine.

2. The process according to claim 1, wherein the pKa of the compound is 7 or less.

3. The process according to claim 2, wherein the compound is a pyridine compound.

4. A process for producing an oxycarbonyl-substituted piperazine derivative comprising oxycarbonylating a piperazine derivative represented by formula (1) in the presence of a reagent comprising benzyl chlorocarbonate or di-tert-butyl dicarbonate and an organic alcohol solvent with a water content of 15 wt % or less to produce an oxycarbonyl-substituted piperazine derivative represented by formula (2)

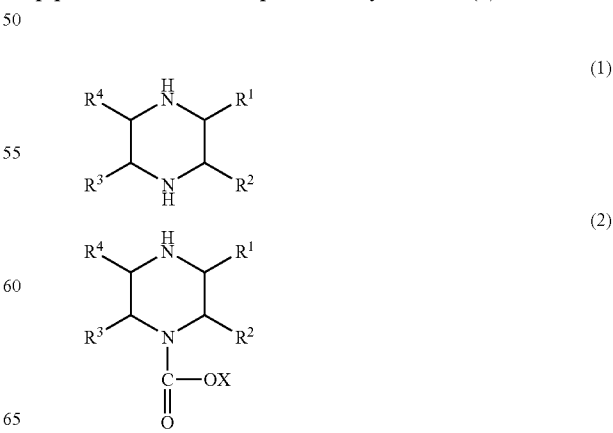

wherein the $R^1$ in the formula (1) and the formula (2) denotes a methyl group, and $R^2, R^3$ and $R^4$ denote a hydrogen atom respectively; X denotes a tert-butyl group or benzyl group; and the compounds represented by the formula (1) and the formula (2) are optically active substances, wherein the piperazine derivative represented by formula (1) is a diastereomer salt of an optically active piperazine derivative and an optically active resolving agent, obtained by optical resolution using the optically active resolving agent, or the optically active piperazine derivative obtained by decomposing the salts.

5. The process according to claim 4, wherein the optically active piperazine derivative obtained by optical resolution with a solvent which is 0.5 to 4.0 times as heavy as a racemic piperazine derivative in the presence of a lower carboxylic acid or mineral acid is used as the raw material.

6. The process according to claim 4 or 5, wherein the optically active resolving agent is optically active tartaric acid.

7. The process according to claim 5, wherein the lower carboxylic acid or mineral acid is at least one selected from acetic acid, propionic acid, hydrochloric acid and sulfuric acid.

8. The process according to claim 5, wherein the solvent used for performing optical resolution is water or a alcohol.

9. The process according to claim 4, further comprising decomposing the diastereomer salts obtained by optical resolution from an optically active water soluble piperazine derivative and optically active tartaric acid with a salt of an alkaline earth metal is used in a solvent containing 50 wt % or more of water.

10. The process according to claim 9, wherein the salt of an alkaline earth metal is any one of hydroxides, halides, sulfates and carbonates.

11. The process according to claim 10, wherein the hydroxide of an alkaline earth metal is any one of magnesium hydroxide, calcium hydroxide, strontium hydroxide and barium hydroxide.

12. The process according to claim 1 or 4, wherein the oxycarbonyl-substituted piperazine derivative is refined by
  (1) a step of washing using an organic solvent whose mutual solubility with water at 20° C. is 10 wt % or less in a water solvent whose pH is 3 or less, and/or
  (2) a distillation step.

13. The process according to claim 12, wherein the organic solvent whose mutual solubility with water at 20° C. is 10 wt % or less is an aromatic hydrocarbon.

* * * * *

UNITED STATES PATENT AND TRADEMARK OFFICE
CERTIFICATE OF CORRECTION

PATENT NO. : 7,569,690 B2
APPLICATION NO. : 10/524517
DATED : August 4, 2009
INVENTOR(S) : Morimoto et al.

It is certified that error appears in the above-identified patent and that said Letters Patent is hereby corrected as shown below:

In Column 2
At line 45, after "Summary", please insert:
-- We provide a process for producing an oxycarbonyl-substituted piperazine derivative, in which a piperazine derivative represented by general formula (1) is oxycarbonylated to produce an oxycarbonyl-substituted piperazine derivative represented by general formula (2) --;

and after the formula 2, please insert:
-- (where $R^1$, $R^2$, $R^3$ and $R^4$ denote, respectively independently, i) a hydrogen atom, ii) an alkyl group with 1 to 4 carbon atoms, iii) an alkoxy group with 1 to 4 carbon atoms, iv) a halogen group, v) a carboxyl group, vi) a carbamoyl group, or vii) an N-alkylcarbamoyl group with 1 to 4 carbon atoms in its alkyl group; X denotes i) an alkyl group with 1 to 4 carbon atoms, ii) an alkenyl group with 2 to 4 carbon atoms, iii) an alkynyl group with 2 to 4 carbon atoms, iv) an aralkyl group not substituted in the aromatic ring, or substituted by an alkyl group with 1 to 4 carbon atoms or by an alkyoxy group with 1 to 4 carbon atoms or by a halogen group, or v) an aryl group not substituted in the aromatic ring, or substituted by an alkyl group with 1 to 4 carbon atoms or by an alkoxy group with 1 to 4 carbon atoms or by a halogen group; excluding the case where all of $R^1$, $R^2$, $R^3$ and $R^4$ denote a hydrogen atom respectively), characterized in that an organic solvent with a water content of 15 wt% or less is used. The oxycarbonyl-substituted piperazine derivative can also be a racemic modification or optically active substance. --

In Column 18
At line 61, please change "{A1/(A1+A2+A3+A4+A5)x100(%)" to {(A2+A3+A4+A5)/(A1+A2+A3+A4+A5)x100(%) --.

Column 24
At line 41, please change "26" to -- 26° C --.

In Column 26
At line 45, please change "26" to -- 26° C --.

Signed and Sealed this

Fourteenth Day of September, 2010

David J. Kappos
*Director of the United States Patent and Trademark Office*